(12) United States Patent
Bossenmaier et al.

(10) Patent No.: US 7,405,231 B2
(45) Date of Patent: *Jul. 29, 2008

(54) OXIDIZED THIOETHER DERIVATIVES

(75) Inventors: Birgit Bossenmaier, Seefeld (DE); Walter-Gunar Friebe, Mannheim (DE); Thomas Friess, Planegg (DE); Lothar Kling, Mannheim (DE); Matthias Rueth, Penzberg (DE); Edgar Voss, Bichl (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 454 days.

This patent is subject to a terminal disclaimer.

(21) Appl. No.: 11/073,065

(22) Filed: Mar. 4, 2005

(65) Prior Publication Data
US 2005/0203064 A1 Sep. 15, 2005

(30) Foreign Application Priority Data
Mar. 5, 2004 (EP) ................... 04005274

(51) Int. Cl.
*A61K 31/41* (2006.01)
*C07D 249/04* (2006.01)
(52) U.S. Cl. ...................... 514/359; 548/255
(58) Field of Classification Search ................ 514/359; 548/255
See application file for complete search history.

(56) References Cited

U.S. PATENT DOCUMENTS 7,163,953 B2 * 1/2007 Bossenmaier et al. ....... 514/374
7,235,574 B2 * 6/2007 Bossenmaier et al. ....... 514/374

FOREIGN PATENT DOCUMENTS

| EP | 1270571 | 1/2003 |
| WO | WO 98/03505 | 1/1998 |
| WO | WO 01/77107 | 10/2001 |
| WO | WO 03/031442 | 4/2003 |
| WO | WO 03/059907 | 7/2003 |

OTHER PUBLICATIONS

Copending U.S. Appl. No. 11/083,176.*
Wilks et al., Progress in Growth Factor Research, 2, pp. 97-111 (1990).
Chan et a., Cur. Opin. in Immunol., 8, pp. 394-401 (1995).
Yarden et al., Ann. Rev. Biochem., 57, pp. 443-478 (1988).
Wright et al., Br. J. Cancer, 65, pp. 118-121 (1992).
Baselga et al., Oncology, 63 (Suppl. 1), pp. 6-16 (2002).
Ranson et al., Oncology, 63 (Suppl. 1), pp. 17-24 (2002).

* cited by examiner

*Primary Examiner*—Golam M. M. Shameem
*Assistant Examiner*—Susannah Chung
(74) *Attorney, Agent, or Firm*—George W. Johnston; Patricia S. Rocha-Tramaloni; Gene J. Yao

(57) ABSTRACT

The present invention provides the compounds of formula I

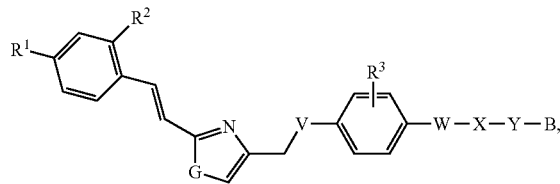

formula I their pharmaceutically acceptable salts or esters, enantiomeric forms, diastereoisomers and racemates, the preparation of the above-mentioned compounds, pharmaceutical compositions containing them and their manufacture, as well as the use of the above-mentioned compounds in the control or prevention of illnesses such as cancer.

18 Claims, No Drawings

OXIDIZED THIOETHER DERIVATIVES

PRIORITY TO RELATED APPLICATIONS

This application claims the benefit of European Application No. 04005274.8, filed Mar. 5, 2004, which is hereby incorporated herein by reference in its entirety.

FIELD OF THE INVENTION

The present invention relates to novel oxidized thioether derivatives, to a process for their manufacture, pharmaceutical compositions containing them and their manufacture as well as the use of these compounds as pharmaceutically active agents for the prevention or treatment of cancer.

BACKGROUND OF THE INVENTION

Protein tyrosine kinases (PTKs) catalyze the phosphorylation of tyrosyl residues in various proteins involved in the regulation of cell growth and differentiation (Wilks et al., Progress in Growth Factor Research 97 (1990) 2; Chan, A. C., and Shaw, A. S., Curr. Opin. Immunol. 8 (1996) 394-401). Such PTKs can be divided into receptor tyrosine kinases (e.g. EGFR/HER-1, c-erB2/HER-2, c-met, PDGFr, FGFr) and non-receptor tyrosine kinases (e.g. src, lck). It is known that many oncogenes encode proteins which are aberrant tyrosine kinases capable of causing cell transformation (Yarden, Y., and Ullrich, A., Annu. Rev. Biochem. 57 (1988) 443-478; Larsen et al., Ann. Reports in Med. Chem., 1989, Chpt. 13). Also over-expression of a normal proto-oncogenic tyrosine kinase may result in proliferative disorders.

It is known that receptor tyrosine kinases of the HER-family like HER-2 and EGFR (HER-1) are frequently aberrantly expressed in common human cancers such as breast cancer, gastrointestinal cancer such as colon, rectal or stomach cancer, leukemia and ovarian, bronchial and pancreatic cancer. High levels of these receptors correlate with poor prognosis and response to treatment (Wright, C., et al., Br. J. Cancer 65 (1992) 118-121).

Accordingly, it has been recognized that inhibitors of receptor tyrosine kinases are useful as selective inhibitors of the growth of mammalian cancer cells. Therefore several small molecule compounds as well as monoclonal antibodies are in clinical trials for the treatment of various types of cancer (Baselga, J., and Hammond, L. A., Oncology 63 (Suppl. 1) (2002) 6-16; Ranson, M., and Sliwkowski, M. X., Oncology 63 (Suppl. 1) (2002) 17-24).

Some substituted oxazoles are known in the art. WO 98/03505, EP 1 270 571, WO 01/77107, WO 03/031442 and WO 03/059907 disclose related heterocyclic compounds as—tyrosine kinase inhibitors.

However there remains a need for new compounds with improved therapeutic properties, such as enhanced activity, decreased toxicity, better solubility and improved pharmacokinetic profile, to name only a few.

SUMMARY OF THE INVENTION

The present invention relates to new compounds of the general formula I, formula I wherein:
- $R^1$ is —S(O)CH$_3$, —S(O)CF$_3$, S(O)$_2$CH$_3$, or S(O)$_2$CF$_3$;
- $R^2$ is hydrogen, fluorine, or chlorine;
- $R^3$ is hydrogen, (C$_1$—C$_3$)alkyl, (C$_1$—C$_3$)alkoxy, or halogen;
- G is —NH—, —S—, or —O—;
- V is —O— or —S(O)$_x$—;
- W is —CH$_2$— or a direct bond;
- X is —NH—, —O—, —S(O)$_x$—, —C(O)—, —C(O)NH—, —NHC(O)—, —S(O)$_2$NH—, —NHS(O)$_2$—, —CH=CH—, C≡C—, or —CH$_2$—;
- Y is —(CH$_2$)$_n$—;
- B is selected from the group consisting of:
  - (a) imidazolyl, which is:
    - (1) unsubstituted; or
    - (2) once substituted with —C(O)OH; or
    - (3) one, two or three times substituted with alkyl, which alkyl is:
      - (A) optionally interrupted one, two, or three times by —O—, —S(O)$_x$—, —S(O)$_2$NH—, —NHS(O)$_2$—, —C(O)—NH—, —NH—C(O)—, or —P(O)(CH$_3$)—; and
      - (B) unsubstituted or one, two or three times substituted with —OH, —NH$_2$, —C(O)OH, or —P(O)(CH$_3$)$_2$; or
    - (4) once substituted with —C(O)OH and one, two or three times substituted with alkyl, which alkyl is:
      - (A) optionally interrupted one, two, or three times by —O—, —S(O)$_x$—, —S(O)$_2$NH—, —NHS(O)$_2$—, —C(O)—NH—, —NH—C(O)—, or —P(O)(CH$_3$)—; and
      - (B) unsubstituted or one, two or three times substituted with —OH, —NH$_2$, —C(O)OH, or —P(O)(CH$_3$)$_2$;
  - (b) pyrazolyl, which is:
    - (1) unsubstituted; or
    - (2) once substituted with —C(O)OH; or
    - (3) one, two or three times substituted with alkyl, which alkyl is:
      - (A) optionally interrupted one, two, or three times by —O—, —S(O)$_x$—, —S(O)$_2$NH—, —NHS(O)$_2$—, —C(O)—NH—, —NH—C(O)—, or —P(O)(CH$_3$)—; and
      - (B) unsubstituted or one, two or three times substituted with —OH, —NH$_2$, —C(O)OH, or —P(O)(CH$_3$)$_2$; or
    - (4) once substituted with —C(O)OH and one, two or three times substituted with alkyl, which alkyl is:
      - (A) optionally interrupted one, two, or three times by —O—, —S(O)$_x$—, —S(O)$_2$NH—, —NHS(O)$_2$—, —C(O)—NH—, —NH—C(O)—, or —P(O)(CH$_3$)—; and (B) unsubstituted or one, two or three times substituted with —OH, —NH$_2$, —C(O)OH, or —P(O)(CH$_3$)$_2$;
(c) triazolyl, which is:
(1) unsubstituted; or
(2) once substituted with —C(O)OH; or
(3) one, two or three times substituted with alkyl, which alkyl is:
(A) optionally interrupted one, two, or three times by —O—, —S(O)$_x$—, —S(O)$_2$NH—, —NHS(O)$_2$—, —C(O)—NH—, —NH—C(O)—, or —P(O)(CH$_3$)—; and
(B) unsubstituted or one, two or three times substituted with —OH, —NH$_2$, —C(O)OH, or —P(O)(CH$_3$)$_2$; or
(4) once substituted with —C(O)OH and one, two or three times substituted with alkyl, which alkyl is:
(A) optionally interrupted one, two, or three times by —O—, —S(O)$_x$—, —S(O)$_2$NH—, —NHS(O)$_2$—, —C(O)—NH—, —NH—C(O)—, or —P(O)(CH$_3$)—; and
(B) unsubstituted or one, two or three times substituted with —OH, —NH$_2$, —C(O)OH, or —P(O)(CH$_3$)$_2$; and
(d) tetrazolyl, which is:
(1) unsubstituted; or
(2) once substituted with —C(O)OH; or
(3) one, two or three times substituted with alkyl, which alkyl is:
(A) optionally interrupted one, two, or three times by —O—, —S(O)$_x$—, —S(O)$_2$NH—, —NHS(O)$_2$—, —C(O)—NH—, —NH—C(O)—, or —P(O)(CH$_3$)—; and
(B) unsubstituted or one, two or three times substituted with —OH, —NH$_2$, —C(O)OH, or —P(O)(CH$_3$)$_2$; or
(4) once substituted with —C(O)OH and one, two or three times substituted with alkyl, which alkyl is:
(A) optionally interrupted one, two, or three times by —O—, —S(O)$_x$—, —S(O)$_2$NH—, —NHS(O)$_2$—, —C(O)—NH—, —NH—C(O)—, or —P(O)(CH$_3$)—; and
(B) unsubstituted or one, two or three times substituted with —OH, —NH$_2$, —C(O)OH, or —P(O)(CH$_3$)$_2$;
n is 1, 2 or 3;
x is 0, 1 or 2; and
pharmaceutically acceptable salts or esters thereof.

In one particular embodiment, B is an imidazolyl as defined above. In another particular embodiment, B is a pyrazolyl as defined above. In a further particular embodiment, B is a triazolyl as defined above; and in another specific embodiment of the invention, B is a tetrazolyl as defined above.

The compounds of the present invention show activity as inhibitors of the HER-signaling pathway and therefore possess anti-proliferative activity. These compounds are useful for preventing or treating proliferative diseases and conditions such as tumor growth and cancer including, but not limited to, breast cancer, leukemia, ovarian cancer, bronchial or lung cancer, pancreatic cancer, and gastrointestinal cancer such as colon cancer, rectal cancer, and stomach cancer.

The compounds of the present invention include the compounds of formula I and their pharmaceutically acceptable salts or esters, enantiomeric forms, diastereoisomers and racemates, the preparation of the above-mentioned compounds, compositions containing them and their manufacture as well as the use of the above-mentioned compounds in the control or prevention of illnesses, especially of illnesses and disorders as mentioned above or in the manufacture of corresponding pharmaceutical compositions.

DETAILED DESCRIPTION OF THE INVENTION

As used herein, the term "(C$_1$-C$_3$)alkyl" means a linear or branched, saturated hydrocarbon with 1, 2 or 3 carbon atoms. Examples are methyl, ethyl, propyl or isopropyl.

As used herein, the term "(C$_1$-C$_3$)alkoxy" means a (C$_1$-C$_3$) alkyl group as defined above, which is attached via an oxygen-atom (i.e., —O-alkyl such as methoxy, ethoxy, etc.).

As used herein, the term "alkyl" denotes a linear or branched, saturated hydrocarbon with 1 to 6, preferably 1 to 4 and more preferably 1 or 2 carbon atoms. Preferred "alkyl" groups are methyl, ethyl, propyl, isopropyl, n-butyl, 2-butyl, tert-butyl and the like. Preferred substituted "alkyl" groups are for example 2-(2-hydroxyethoxy)ethyl, 1-hydroxyethyl, 2-hydroxyethyl, 2-(2-methoxy-ethoxy)-ethyl, hydroxymethyl, 2-methanesulfinyl-ethyl, 2-methanesulfonyl-ethyl, dimethyl-phosphinoylmethyl, methoxymethyl, carboxymethyl, 2-carboxyethyl, aminomethyl, 1-aminoethyl, 2-aminoethyl and the like. In addition, the present invention provides alkyls which may optionally be interrupted one, two or three times by —O—, —S(O)$_x$,-, —S(O)$_2$NH$_2$—, —NH$_2$S(O)$_2$—, or —P(O)(CH$_3$)— and may be unsubstituted or one, two or three times substituted with —OH, —NH$_2$, —C(O)OH or —P(O)(CH$_3$)$_2$.

The imidazole, pyrazole, triazole or tetrazole as used herein may be attached to the group —W—X—Y— of formula I via any suitable carbon- or nitrogen atom. They may further be unsubstituted, once substituted by —C(O)OH and/or one, two or three times substituted with "alkyl". Examples are 1H-[1,2,3]triazol-1-yl; 1H-[1,2,3]triazol-5-yl; 1H-imidazol-1-yl; 1H-tetrazol-5-yl; 2-(2-hydroxyethyl)-1H-imidazol-1-yl; 2-(2-aminoethyl)-1H-imidazol-1-yl; 2-ethoxyethyl-1H-imidazol-1-yl; 2-[2-(dimethyl-phosphinoyl)-ethyl]-1H-imidazol-1-yl and the like.

As used herein, the term "halogen" denotes fluorine, chlorine, bromine and iodine, preferably fluorine or chlorine.

As used herein the term "proliferative disease" means a cell proliferative disease such as an inflammatory disease (e.g., rheumatoid arthritis) or in particular, oncological diseases such as, but not limited to, tumor growth or cancer including breast cancer, leukemia, ovarian cancer, bronchial or lung cancer, pancreatic cancer, and gastrointestinal cancer such as colon cancer, rectal cancer, and stomach cancer.

As used herein, when referring to the receptor tyrosine kinases of the HER-family like HER-2 and EGFR (HER-1), the acronym "HER" refers to human epidermal receptor and the acronym "EGFR" refers to epidermal growth factor receptor.

As used herein, "THF" refers to tetrahydrofuran.

As used herein, the term "DMF" refers to N,N-dimethylformamide.

As used herein, the term "r.t." refers to room temperature.

As used herein, the term "FCS" refers to Fetal Calf Serum.

As used herein, the term "EGTA" refers to Ethylene glycol-bis(2-aminoethylether)-N,N,N',N'-tetraacetic acid.

As used herein, the term "Hepes" refers to 4-(2-Hydroxyethyl)-1-piperazineethanesulfonic acid.

As used herein, the term "PMSF" refers to Phenylmethylsulfonyl fluoride.

As used herein, the term "Aprotinin" refers to a naturally occurring protein that is obtained and purified from cow's lungs.

As used herein, the term "Orthovanadate" refers to $Na_3VO_4$.

As used herein, the term "DMSO" refers to N,N-dimethylsulfoxide.

As used herein, the term "pY 1248" refers to the phosphorylated tyrosine residue 1248 of human epidermal receptor 2.

As used herein, "NSCLC" (e.g. QG56, A549, Calu-3) refers to Non-Small-Cell Lung Cancer.

As used herein, the term "NCI" refers to the National Cancer Institute.

As used herein, "Lactose Anhydrous DTG" refers to anhydrous lactose in direct tabletting grade.

As used herein, in relation to mass spectrometry (MS) the term "ESI+" refers to positive electrospray ionization mode; the term "APCI+" and "APCI−" refer to positive and negative atmospheric pressure chemical ionization mode and the term "M+" refers to the positive molecular mass ion peak of the ionized molecule.

As used herein, in relation to nuclear magnetic resonance (NMR) the term "$D_6$-DMSO" refers to deuterated N,N-dimethylsulfoxide and the term "$\underline{CDCl_3}$" refers to deuterated chloroform.

As used herein, the term "Triton" refers to octylphenol ethoxylate.

As used herein, the term "DMPU" refers to 1,3-Dimethyl-3,4,5,6-tetrahydro-2(1H)-pyrimidinone.

As used herein, the term "HPLC-MS" refers to high-performance liquid chromatography-mass spectrometry.

As used herein, the term "content according to GC/FID" refers to the purity according to a measurement with gas chromatography with a flame ion detector.

As used herein, the term "a therapeutically effective amount" of a compound means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated.

In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

As used herein, a "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention are contemplated. Supplementary active compounds can also be incorporated into the compositions.

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, benzenesulfonic acid, naphthalenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and quaternary ammonium hydroxides, such as for example, tetramethylammonium hydroxide. The chemical modification of a pharmaceutical compound (i.e. a drug) into a salt is a technique well known to pharmaceutical chemists to obtain improved physical and chemical stability, hygroscopicity, flowability and solubility of compounds. See, e.g., Bastin, R. J. et al, Organic Proc. Res. Dev. 4 (2000) 427-435.

Preferred examples for the group —W—X—Y— are:
—$(CH_2)_4$—; —O—$(CH_2)_3$—; —C(O)—$(CH_2)_3$—; —S—$(CH_2)_3$—;
—S(O)—$(CH_2)_3$—; —$S(O)_2$—NH—$(CH_2)_2$—; —NH—C(O)—$(CH_2)_2$—; —C(O)—NH—$(CH_2)_2$—;
—$CH_2$—NH—$(CH_2)_2$—; —$CH_2$—O—$(CH_2)_2$—; —$CH_2$—S(O)—$(CH_2)_2$—; —$CH_2$—$S(O)_2$—$(CH_2)_2$—; —CH=CH—$CH_2$—; —CH=CH—$(CH_2)_2$—; —$CH_2$—CH=CH—$CH_2$—; and —C≡C—$(CH_2)_2$—, A preferred embodiment of the present invention are the compounds of formula I, wherein:
$R^1$ is —$S(O)CH_3$, —$S(O)CF_3$, $S(O)_2CH_3$ or $S(O)_2CF_3$;
G is —S— or —O—; and
the remaining substituents have the significance given above for formula I; and
pharmaceutically acceptable salts or esters thereof.

Another preferred embodiment of the present invention are the compounds of formula I, wherein:
$R^1$ is —$S(O)CH_3$, —$S(O)CF_3$, $S(O)_2CH_3$ or $S(O)_2CF_3$;
$R^2$ is hydrogen;
$R^3$ is hydrogen;
G is —S— or —O—;
the remaining substituents have the significance given above for formula I; and
pharmaceutically acceptable salts or esters thereof.

Another preferred embodiment of the present invention are the compounds of formula I, wherein:
$R^1$ is —$S(O)CH_3$; —$S(O)CF_3$; —$S(O)_2CH_3$ or —$S(O)_2CF_3$;
$R^2$ is hydrogen;
$R^3$ is hydrogen or methyl;
G is —O—;
V is —O—;
the remaining substituents have the significance given above for formula I; and
pharmaceutically acceptable salts or esters thereof.

Still a preferred embodiment of the present invention are the compounds of formula I, wherein:
$R^1$ is —S(O)—$CF_3$ or —$S(O)_2CF_3$;
$R^2$ is hydrogen;
$R^3$ is hydrogen;
G is —O— or —S—;
V is —O— or —$S(O)_x$—;
—W—X—Y— is —$(CH_2)_4$—; —O—$(CH_2)_3$—; —C(O)—$(CH_2)_3$—; —S—$(CH_2)_3$—; —$S(O)_2$—$(CH_2)_3$—; —S(O)—$(CH_2)_3$—; —$S(O)_2$—NH—

$(CH_2)_2$—; —NH—C(O)—$(CH_2)_2$—; —C(O)—NH—$(CH_2)_2$—; —$CH_2$—NH—$(CH_2)_2$—; —$CH_2$—O—$(CH_2)_2$—; —$CH_2$—; —$CH_2$—$S(O)_2$—$(CH_2)_2$—; —CH=CH—$CH_2$—; —CH=CH—$(CH_2)_2$—; —$CH_2$—CH=CH—$CH_2$—; or —C≡C—$(CH_2)_2$—;

B is selected from the group consisting of:
(a) imidazolyl, which is:
  (1) unsubstituted; or
  (2) one, two or three times substituted with alkyl, which alkyl is:
    (A) optionally interrupted one, two, or three times by —O—, —$S(O)_x$—, —$S(O)_2NH$—, —$NHS(O)_2$—, —C(O)—NH—, —NH—C(O)—, or —P(O)($CH_3$)—; and
    (B) unsubstituted or one, two or three times substituted with —OH, —$NH_2$, —C(O)OH, or —P(O)($CH_3$)$_2$; and
(b) triazolyl, which is:
  (1) unsubstituted; or
  (2) one, two or three times substituted with alkyl, which alkyl is:
    (A) optionally interrupted one, two, or three times by —O—, —$S(O)_x$—, —$S(O)_2NH$—, —$NHS(O)_2$—, —C(O)—NH—, —NH—C(O)—, or —P(O)($CH_3$)—; and
    (B) unsubstituted or one, two or three times substituted with —OH, —$NH_2$, —C(O)OH, or —P(O)($CH_3$)$_2$; and
(c) tetrazolyl, which is:
  (1) unsubstituted; or
  (2) one, two or three times substituted with alkyl, which alkyl is:
    (A) optionally interrupted one, two, or three times by —O—, —$S(O)_x$—, —$S(O)_2NH$—, —$NHS(O)_2$—, —C(O)—NH—, —NH—C(O)—, or —P(O)($CH_3$)—; and
    (B) unsubstituted or one, two or three times substituted with —OH, —$NH_2$, —C(O)OH, or —P(O)($CH_3$)$_2$;

x is 0, 1 or 2; and
pharmaceutically acceptable salts or esters thereof.

In a more specific embodiment of the preceding preferred embodiment, B is an imidazolyl. In another specific embodiment of the preceding preferred embodiment B is a triazolyl. In a further specific embodiment of the preceding preferred embodiment B is a tetrazolyl.

Such compounds are for example:
1-[4-(4-{2-[(E)-2-(4-trifluoromethanesulfinyl-phenyl)-vinyl]-thiazol-4-ylmethoxy}-phenyl)-butyl]-1H-[1,2,3]triazole; and
1-[4-(4-{2-[2-(4-trifluoromethanesulfinyl-phenyl)-vinyl]-oxazol-4-ylmethanesulfonyl}-phenyl)-butyl]-1H-[1,2,3]triazole.

Still a preferred embodiment of the present invention are the compounds of formula I, wherein:
$R^1$ is S(O)—$CH_3$ or —$S(O)_2CH_3$;
$R^2$ is hydrogen;
$R^3$ is hydrogen;
G is —O— or —S—;
V is —O—, or —$S(O)_x$—;
—W—X—Y— is —$(CH_2)_4$—; —O—$(CH_2)_3$—; —C(O)—$(CH_2)_3$—; —S—$(CH_2)_3$—; —$S(O)_2$—$(CH_2)_3$—; —$S(O)_2$—$(CH_2)_3$—; —$S(O)_2$—NH—$(CH_2)_2$—; —NH—C(O)—$(CH_2)_2$—; —C(O)—NH—$(CH_2)_2$—; —$CH_2$—NH—$(CH_2)_2$—; —$CH_2$—O—$(CH_2)_2$—; —$CH_2$—S(O)—$(CH_2)_2$—; —$CH_2$—$S(O)_2$—$(CH_2)_2$—; —CH=CH—$CH_2$—; —CH=CH—$(CH_2)_2$—; —$CH_2$—CH=CH—$CH_2$—; or —C≡C—$(CH_2)_2$—;

B is selected from the group consisting of:
(a) imidazolyl, which is:
  (1) unsubstituted; or
  (2) one, two or three times substituted with alkyl, which alkyl is:
    (A) optionally interrupted one, two, or three times by —O—, —$S(O)_x$—, —$S(O)_2NH$—, —$NHS(O)_2$—, —C(O)—NH—, —NH—C(O)—, or —P(O)($CH_3$)—; and
    (B) unsubstituted or one, two or three times substituted with —OH, —$NH_2$, —C(O)OH, or —P(O)($CH_3$)$_2$;
(b) triazolyl, which is:
  (1) unsubstituted; or
  (2) one, two or three times substituted with alkyl, which alkyl is:
    (A) optionally interrupted one, two, or three times by —O—, —$S(O)_x$—, —$S(O)_2NH$—, —$NHS(O)_2$—, —C(O)—NH—, —NH—C(O)—, or —P(O)($CH_3$)—; and
    (B) unsubstituted or one, two or three times substituted with —OH, —$NH_2$, —C(O)OH, or —P(O)($CH_3$)$_2$; and
(c) tetrazolyl, which is:
  (1) unsubstituted; or
  (2) one, two or three times substituted with alkyl, which alkyl is:
    (A) optionally interrupted one, two, or three times by —O—, —$S(O)_x$—, —$S(O)_2NH$—, —$NHS(O)_2$—, —C(O)—NH—, —NH—C(O)—, or —P(O)($CH_3$)—; and
    (B) unsubstituted or one, two or three times substituted with —OH, —$NH_2$, —C(O)OH, or —P(O)($CH_3$)$_2$;

x is 0, 1 or 2; and
pharmaceutically acceptable salts or esters thereof.

In a more specific embodiment of the preceding preferred embodiment, B is an imidazolyl. In another specific embodiment of the preceding preferred embodiment B is a triazolyl. In a further specific embodiment of the preceding preferred embodiment B is a tetrazolyl.

Such a compound is for example:
1-[4-(4-{2-[(E)-2-(4-Methanesulfinyl-phenyl)-vinyl]-oxazol-4-ylmethoxy}-phenyl)-butyl]-1H-[1,2,3]triazole.

Another preferred embodiment of the present invention are the compounds of formula I, wherein:
$R^1$ is —S(O)—$CF_3$;
$R^2$ and $R^3$ are both hydrogen;
G and V are both —O—;
—W—X—Y— is —$(CH_2)_4$—; —O—$(CH_2)_3$—; —$S(O)_2$—NH—$(CH_2)_2$—; —$CH_2$—O—$(CH_2)_2$—; —$CH_2$—S(O)—$(CH_2)_2$—; —$CH_2$—$S(O)_2$—$(CH_2)_2$—; —CH=CH—$(CH_2)_2$— or —C≡C—$(CH_2)_2$—;

B is selected from the group consisting of:
(a) unsubstituted triazolyl;
(b) unsubstituted tetrazolyl; and
(c) imidazolyl which is (1) unsubstituted or (2) once substituted with 2-(2-hydroxyethoxy)ethyl, 1-hydroxyethyl, 2-hydroxyethyl, 2-(2-methoxy-ethoxy)-ethyl, hydroxymethyl, 2-methanesulfinyl-ethyl, 2-methanesulfonyl-ethyl, dimethyl-phosphinoylmethyl, methoxymethyl, carboxymethyl, 2-carboxyethyl, aminomethyl, 1-aminoethyl, or 2-aminoethyl; and pharmaceutically acceptable salts or esters thereof.

In a more specific embodiment of the preceding preferred embodiment, B is an unsubstituted triazolyl. In another specific embodiment of the preceding preferred embodiment, B is an unsubstituted tetrazolyl. In a further specific embodiment of the preceding preferred embodiment, B is an imidazolyl as defined above.

Such compounds are for example:

4-[4-(4-imidazol-1-yl-butyl)-phenoxymethyl]-2-[2-(4-trifluoromethanesulfinyl-phenyl)-vinyl]-oxazole;

2-{1-[4-(4-{2-[(E)-2-(4-trifluoromethanesulfinyl-phenyl)-vinyl]-oxazol-4-ylmethoxy}phenyl)-butyl]-1H-imidazol-2-yl}-ethanol;

(2-[1,2,3]triazol-1-yl-ethyl)-(4-{2-[(E)-2-(4-trifluoromethanesulfinyl-phenyl)-vinyl]-oxazol-4-ylmethoxy}-benzyl)-amine;

1-[4-(4-{2-[2-(4-trifluoromethanesulfinyl-phenyl)-vinyl]-oxazol-4-ylmethoxy}-phenyl)-butyl]-1H-[1,2,3]triazole;

4-[4-(4-{2-[(E)-2-(4-trifluoromethanesulfinyl-phenyl)-vinyl]-oxazol-4-ylmethoxy}-phenyl)-butyl]-1H-[1,2,3]triazole;

5-[4-(4-{2-[(E)-2-(4-trifluoromethanesulfinyl-phenyl)-vinyl]-oxazol-4-ylmethoxy}-phenyl)-butyl]-2H-tetrazole;

1-[2-(4-{2-[-4-(trifluoromethanesulfinyl-phenyl)-vinyl]-oxazol-4-ylmethoxy}-benzyloxy)-ethyl]-1H-[1,2,3]-triazole;

1-[2-(4-{2-[(E)-2-(4-trifluoromethanesulfinyl-phenyl)-vinyl]-oxazol-4-ylmethoxy}-phenylmethanesulfinyl)-ethyl]-1H-[1,2,3]triazole;

1-[2-(4-{2-[(E)-2-(4-trifluoromethanesulfinyl-phenyl)-vinyl]-oxazol-4-ylmethoxy}-phenylmethanesulfonyl)-ethyl]-1H-[1,2,3]triazole;

1-[4-(4-{2-[2-(4-trifluoromethanesulfinyl-phenyl)-vinyl]-oxazol-4-ylmethoxy}-phenyl)-but-3-enyl]-1H-[1,2,3]triazole;

1-[4-(4-{2-[2-(4-trifluoromethanesulfinyl-phenyl)-vinyl]-oxazol-4-ylmethoxy}-phenyl)-but-3-ynyl]-1H-[1,2,3]triazole;

N-(2-[1,2,3]triazol-1-yl-ethyl)-4-{2-[(E)-2-(4-trifluoromethanesulfinyl-phenyl)-vinyl]-oxazol-4-ylmethoxy}-benzenesulfonamide; and 1-[3-(4-{2-[2-(4-trifluoromethanesulfinyl-phenyl)-vinyl]-oxazol-4-ylmethoxy}-phenoxy)-propyl]-1H-[1,2,3]triazole.

Another preferred embodiment of the present invention are the compounds of formula I, wherein:

$R^1$ is —S(O)$_2$—CF$_3$;

$R^2$ and $R^3$ are both hydrogen;

G and V are both —O—;

—W—X—Y— is —(CH$_2$)$_4$—, —O—(CH$_2$)$_3$—, —S(O)$_2$—NH—(CH$_2$)$_2$—, —CH$_2$—NH—(CH$_2$)$_2$—, —CH$_2$—O—(CH$_2$)$_2$—, —CH$_2$—S(O)—(CH$_2$)$_2$—, —CH$_2$—S(O)$_2$—(CH$_2$)$_2$—, —CH=CH—(CH$_2$)$_2$— or —C≡C—(CH$_2$)$_2$—;

B is triazolyl; and pharmaceutically acceptable salts or esters thereof.

Such compounds are for example:

1-[4-(4-{2-[(E)-2-(4-trifluoromethanesulfonyl-phenyl)-vinyl]-oxazol-4-ylmethoxy}-phenyl)-butyl]-1H-[1,2,3]triazole; or 1-[2-(4-{2-[(E)-2-(4-trifluoromethanesulfinyl-phenyl)-vinyl]-oxazol-4-ylmethoxy}-phenylmethanesulfinyl)-ethyl]-1H-[1,2,3]triazole.

Another preferred embodiment of the present invention are the compounds of formula I, wherein:

$R^1$ is —S(O)—CF$_3$;

$R^2$ is hydrogen;

$R^3$ is methyl;

G and V are both —O—;

—W—X—Y— is -(CH$_2$)$_4$—, —O—(CH$_2$)$_3$—, —S(O)$_2$—NH—(CH$_2$)$_2$—, —CH$_2$—NH—(CH$_2$)$_2$—, —CH$_2$—O—(CH$_2$)$_2$—, —CH$_2$—S(O)—(CH$_2$)$_2$—, —CH$_2$—S(O)$_2$—(CH$_2$)$_2$—, —CH$_2$—S(O)$_2$—(CH$_2$)$_2$—, —CH=CH—(CH$_2$)$_2$— or —C≡C—(CH$_2$)$_2$—;

B is selected from the group consisting of:
(a) unsubstituted triazolyl or tetrazolyl; and
(b) imidazolyl which is (1) unsubstituted or (2) once substituted with 2-(2-hydroxyethoxy)ethyl, 1-hydroxyethyl, 2-hydroxyethyl, 2-(2-methoxy-ethoxy)-ethyl, hydroxymethyl, 2-methanesulfinyl-ethyl, 2-methanesulfonyl-ethyl, dimethyl-phosphinoylmethyl, methoxymethyl, carboxymethyl, 2-carboxyethyl, aminomethyl, 1-aminoethyl, or 2-aminoethyl; and pharmaceutically acceptable salts or esters thereof.

In a more specific embodiment of the preceding preferred embodiment, B is an unsubstituted imidazolyl. In another specific embodiment of the preceding preferred embodiment, B is a substituted imidazolyl as defined above. In another specific embodiment of the preceding preferred embodiment, B is an unsubstituted tetrazolyl; and in a further specific embodiment of the preceding preferred embodiment, B is an unsubstituted triazoly.

Such a compound is for example:

1-[4-(2-Methyl-4-{2-[(E)-2-(-4-trifluoromethanesulfinyl-phenyl)-vinyl]-oxazol-4-ylmethoxy}-phenyl)-butyl]-1H-[1,2,3]triazole.

Another preferred embodiment of the present invention are the compounds of formula I, wherein:

$R^1$ is —S(O)$_2$—CF$_3$;

$R^2$ is hydrogen;

$R^3$ is methyl;

G and V are both —O—;

—W—X—Y— is —(CH$_2$)$_4$—, —O—(CH$_2$)$_3$—, —S(O)$_2$—NH—(CH$_2$)$_2$—, —CH$_2$—NH—(CH$_2$)$_2$—, —CH$_2$—O—(CH$_2$)$_2$—, —CH$_2$—S(O)—(CH$_2$)$_2$—, —CH$_2$—S(O)$_2$—(CH$_2$)$_2$—, —CH=CH—(CH$_2$)$_2$— or —C≡C—(CH$_2$)$_2$—;

B is triazolyl; and pharmaceutically acceptable salts or esters thereof.

Such a compound is for example:

1-[4-(2-Methyl-4-{2-[(E)-2-(4-trifluoromethanesulfonyl-phenyl)-vinyl]-oxazol-4-ylmethoxy}-phenyl)-butyl]-1H-[1,2,3]triazole.

Still another embodiment of the present invention is a process for the manufacture of the compounds of formula I, wherein:

a) a compound of formula III

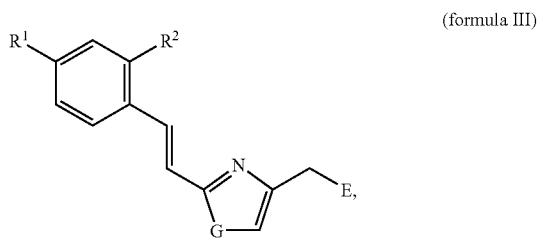

(formula III)

wherein $R^1$, $R^2$ and G have the meaning given for formula I and E denotes a suitable leaving group, is reacted with a compound of formula IV

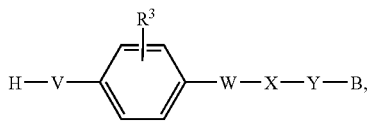

(formula IV)

wherein $R^3$, V, W, X, Y and B have the meaning given for formula I;

b) a protecting group, if present to protect the heteroatoms in the imidazole-, pyrazole-, triazole- or tetrazole ring of "B" from undesired side reactions is cleaved to give a compound of formula I;

c) said compound of formula I is isolated from the reaction mixture; and d) if desired is turned into a pharmaceutically acceptable salt or ester.

The compounds of the general formula I, or a pharmaceutically acceptable salt or ester thereof, may be prepared by any process known to be applicable for the preparation of chemically-related compounds by one skilled in the art. Such processes, when used to prepare the compounds of formula I, or a pharmaceutically-acceptable salt or ester thereof, are provided as a further feature of the invention. Necessary starting materials may be obtained by standard procedures of organic chemistry. The preparation of such starting materials is described within the accompanying non-limiting examples. Alternatively necessary starting materials are obtainable by analogous procedures to those illustrated which are within the ordinary skill of an organic chemist.

In detail, the preparation of the compounds according to the present invention may vary according to the nature of the group —W—X—Y—. Therefore, further embodiments of the present invention are the processes for the manufacture of the compounds of formula I as described below.

In one embodiment, a compound of formula II

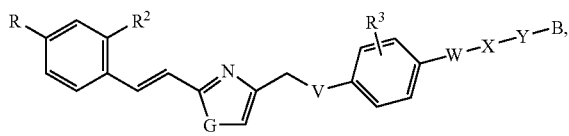

(formula II)

wherein $R^2$, $R^3$, G, V, W, X, Y and B have the meaning given for formula I, and R denotes —S-alkyl, is reacted with a suitable oxidizing agent such as, for example, peracids as described below to convert R into $R^1$.

In a further embodiment, if W in formula I denotes —CH$_2$— and X is —NH— or —O— or —S(O)$_x$—, the corresponding compounds according to the present invention may also be prepared by reacting a compound of formula V

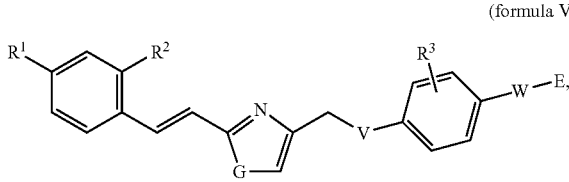

(formula V)

wherein $R^1$, $R^2$, $R^3$, G, V and W have the meanings given for formula I, and E denotes a suitable leaving group as defined below, preferably iodide, bromide or chloride, p-toluenesulfonate (tosylate), methanesulfonate (mesylate), trifluoromethansulfonate (triflate) or the azido group, with a compound of formula VI

   (formula VI), wherein Y and B have the meanings given for formula I, and X' denotes —NH$_2$, —OH or —S(O)$_x$H, wherein x is 0,1 or 2.

In another embodiment, if W in formula I denotes —CH$_2$— and X is —NH—, the corresponding compounds of the present invention may also be prepared by reacting a compound of formula VII

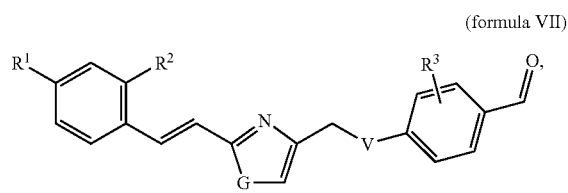

(formula VII)

wherein $R^1$, $R^2$, $R^3$, G and V have the meanings given for formula I, with a compound of formula VIII

   (formula VIII), wherein Y and B have the meanings given before and X" denotes —NH$_2$, under conditions of a reductive amination.

In still another embodiment, if W and X in formula I denote —CH$_2$—, the corresponding compounds according to the present invention may also be prepared by reacting a compound of formula IX

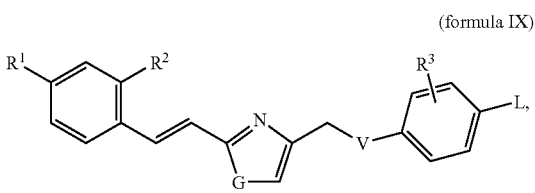

(formula IX)

wherein $R^1$, $R^2$, $R^3$, G and V have the meanings given for formula I, and L denotes halogen or triflate, with a compound of formula X

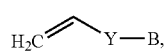

(formula X)

wherein Y and B have the meanings given herein before, and whereby said compound of formula X, prior to its reaction with said compound of formula IX is hydroborated using 9-borobicyclo[3.3.1]nonane and a palladium catalyst, preferably [1,1'-Bis(diphenylphosphino)ferrocene] dichloropalladium(II).

In particular, oxidation of compounds of formula II is preferably carried out in an inert solvent with agents like peracids, e.g. 3-chloro-benzenecarboperoxoic acid in dichloromethane or 2-iodoxybenzoic acid in chloroform or iodosobenzene in toluene to yield the corresponding sulfoxides. Oxidation of compounds of formula II to the corresponding sulfones requires more rigorous conditions, for example periodic acid in acetonitrile under catalysis of chromium(VI) oxide or oxone in aqueous methanol or excess of 3-chloro-benzenecarboperoxoic acid and prolonged reaction time.

The reaction of a compound of formula III with a compound of formula IV, or of a compound of formula V with a compound of formula VI is an alkylation reaction, which is well known to the skilled artisan. Typically, the alkylation may be carried out in solvents like N,N-dimethylformamide (DMF), methanol, ethanol and isopropanol. Typical bases for this reaction are alkaline carbonates, sodium methylate, sodium hydride or lithium diisopropyl amide. The reaction temperatures may vary from 20° C. to 150° C. Preferred alkylation procedures make use of alkaline carbonates as bases in solvents like ketones, for example cesium carbonate in butanone at reflux temperature, or sodium hydride in DMF at room temperature. Suitable leaving groups "E" are those typically used in alkylation reactions and well known to the skilled artisan. Examples of such leaving groups are, among others, the anions of halogens, especially iodide, bromide or chloride, p-toluenesulfonate (tosylate), methanesulfonate (mesylate), trifluoro-methanesulfonate (triflate) or the azido group (See, March, J., Advanced Organic Chemistry, 1992, $4^{th}$ edition, John Wiley & Sons, pages 352-357).

Reaction of a compound of formula VII with a compound of formula VIII under conditions of reductive amination is typically achieved in solvents like acetonitrile, N,N-dimethylformamide, methanol or ethanol and at temperatures between 20° C. and 150° C. Reducing agents typically employed are e.g. sodium cyanoborohydride ($NaCNBH_3$), sodium borohydride ($NaBH_4$) or lithium aluminium hydride ($LiAlH_4$).

Reaction of a compound of formula IX with a compound of formula X is typically achieved in solvents like tetrahydrofuran (THF), N,N-dimethylformamide, acetone or mixtures thereof and at temperatures between 0° C. and 150° C. In a first step, the olefin of formula X is hydroborated, for example with 9-borobicyclo[3.3.1]nonane (9-BBN). Then the resulting boron derivative is coupled to the compound of formula IX using palladium catalysts, for example [1,1'-Bis(diphenylphosphino)ferrocene]dichloropalladium(II) ($PdCl_2(dppf)$), in presence of a base like aqueous cesium carbonate or aqueous sodium carbonate or sodium ethylate.

The reactions described above may require to protect heteroatoms, such as nitrogen in the imidazole, pyrazole, triazole or tetrazole rings of group "B" from undesired side reactions. Therefore, subsequent to any reaction procedure described above, a protecting group if present to protect a hetero atom in an imidazole, pyrazole, triazole or tetrazole group of "B" is removed.

Removal of a protecting group on a hetero atom in group B depends on the nature of such group. However, the use of protection groups in order to protect heteroatoms within an imidazole, pyrazole, triazole or tetrazole of the group "B" from undesired reactions, is within the ordinary skill of an organic chemist. Typical examples are the removal of a trityl group under acidic conditions, for example with aqueous formic acid in THF under reflux or the removal of a substituted silyl group with tetrabutylammonium fluoride in aqueous THF at room temperature.

The compounds of formula I can contain one or several chiral centers and can then be present in a racemic or in an optically active form. The racemates can be separated according to known methods into the enantiomers. For instance, diastereomeric salts which can be separated by crystallization are formed from the racemic mixtures by reaction with an optically active acid such as e.g. D- or L-tartaric acid, mandelic acid, malic acid, lactic acid or camphorsulfonic acid. Alternatively separation of the enantiomers can also be achieved by using chromatography on chiral HPLC-phases which are commercially available.

The compounds of formula I and their pharmaceutically acceptable salts or esters possess valuable pharmacological properties. It has been found that said compounds inhibit the HER-signaling pathway and show anti-proliferative activity. Consequently the compounds of the present invention are useful in the therapy and/or prevention of illnesses with known over-expression of receptor tyrosine kinases of the HER-family like HER-2 and EGFR (HER-1), especially in the therapy and/or prevention of illnesses mentioned above. The activity of the present compounds as HER-signaling pathway inhibitors is demonstrated by the following biological assay:

Biological Data

Inhibition of HER2 phosphorylation in Calu3 tumor cell line.

$2 \times 10^5$ Calu3 cells per well were plated in a 12-well plate. After 4 days cells were starved for 16 h in DMEM(Dulbecco's Modified Eagle Medium)/0.5% FCS/1% Glutamine. During this time cells were incubated with 1 µM of a compound according to the present invention. Afterwards cells were lysed in lyses buffer containing 1% Triton, 10% Glycerol, 1 mM EGTA, 1.5 mM $MgCl_2$, 150 mM NaCl, 50 mM Hepes pH 7.5, 1 mM PMSF, 10 µg/mL Aprotinin and 0.4 mm Orthovanadate. Cell lysates were analyzed on a SDS PAGE and after transfer to a nitrocellulose membrane detected with a rabbit antibody specifically recognizing the pY 1248 in HER2 (Cell Signaling). After incubation with an anti rabbit antibody coupled to POD (Biorad) (Peroxidase available from Biorad, Munich, Germany) signals were detected by chemiluminescence (ECL,Amersham). Inhibition of HER2 phosphorylation is calculated as percentage of the DMSO treated control. This percentage is calculated according to the following formula: Inhibition in %=100-(Phosphorylated-HER2-Signal of Test Sample* 100/Phosphorylated-HER2-Signal DMSO-control).

With all compounds a significant inhibition of HER2-phosphorylation was detected, with compounds from examples 1, 4, 5, 7 and 15 showing a higher percentage of inhibition of phosphorylation than with 1-[4-(4-{2-[2-(4-trifluoromethyl-phenyl)-vinyl]-oxazol-4-ylmethoxy}-phenyl)-butyl]-1H-[1,2,3]triazole (Example 4, p. 88, WO 01/77107) as reference compound.

TABLE 1

|  | Control (DMSO) | Percent inhibition of HER2-phosphorylation (compound concentration 1 µM) |
| --- | --- | --- |
| reference compound | 0 | 52.3 |
| example 1 | 0 | 92.5 |
| example 4 | 0 | 94.4 |
| example 5 | 0 | 82.9 |
| example 7 | 0 | 52.9 |
| example 15 | 0 | 73.6 |

In order to further assess the activity of the compounds according to the present invention, the following in vivo assay on tumor inhibition can be used:

In vivo assay on tumor inhibition:

To generate primary tumors, NSCLC (e.g. QG56, A549, Calu-3) cells ($4-5.0 \times 10^6$ in a volume of 100 µl) are injected subcutaneously into the left flank of female SCID beige mice (Severe Combined Immunodeficient/beige mice available from Charles River, Sulzfeld, Deutschland) or BALB/c nude mice (BALB/c Nude Spontaneous Mutant Mice [homozygotes] available from Taconic Europe [former M&B A/S (Mollegaard and Bomholtgard Breeding and Research Centre) in Denmark]) using a 1 ml syringe and a 26G needle. The tumor cells are originally obtained from the NCI and deposited in a working cell bank. The cells are thawed and expanded in vitro before use in the experiment. Mice are assigned to the treatment groups 14-21 days after cell injection. For grouping (n=10-15 mice per group), the animals are randomized to get a similar mean primary tumor volume of ca. 100-150 mm$^3$ per group. The test compounds are administered orally once per day as a suspension in 7.5% gelatine 0.22% NaCl with an administration volume of 10 ml/kg based on actual body weights. Treatment is initiated one day after staging, and carried out until day 20-50, the final day of the study. The subcutaneous primary tumors are measured twice weekly, starting prior to randomization, in two dimensions (length and width) using an electronic caliper. The volume of the primary tumor is calculated using the formula: V[mm$^3$]= (length [mm]×width [mm]×width [mm])/2. In addition, the body weight of all animals is recorded at least twice weekly. Finally, at the end of the study the tumors are explanted and weighed.

The compounds according to this invention and their pharmaceutically acceptable salts or esters can be used as medicaments, e.g. in the form of pharmaceutical composition. The pharmaceutical compositions can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions.

The above-mentioned pharmaceutical compositions can be obtained by processing the compounds according to this invention with pharmaceutically inert, inorganic or organic carriers. Lactose, corn starch or derivatives thereof, talc, stearic acids or its salts and the like can be used, for example, as such carriers for tablets, coated tablets, dragées and hard gelatine capsules. Suitable carriers for soft gelatine capsules can include, for example, vegetable oils, waxes, fats, semi-solid and liquid polyols and the like. However, depending on the nature of the active substance, carriers may not be required for some soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Preferred pharmaceutical compositions comprise the following:

| a) Tablet formulation (wet granulation): | | | | | |
|---|---|---|---|---|---|
| Item | Ingredients | | Mg/tablet | | |
| 1. | Compound of formula I | 5 | 25 | 100 | 500 |
| 2. | Lactose Anhydrous DTG | 125 | 105 | 30 | 150 |
| 3. | Sta-Rx 1500 (a pre-gelatinized starch powder) | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure:
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

| b) Capsule formulation: | | | | | |
|---|---|---|---|---|---|
| Item | Ingredients | | mg/capsule | | |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure:
1. Mix items 1, 2 and 3 in a suitable mixer for 30 minutes.
2. Add items 4 and 5 and mix for 3 minutes.
3. Fill into a suitable capsule.

c) Microsuspension
1. Weigh 4.0 g glass beads in custom made tube GL 25, 4 cm (the beads fill half of the tube).
2. Add 50 mg compound, disperse with spatulum and vortex.
3. Add 2 ml gelatin solution (weight beads: gelatin solution=2:1) and vortex.
4. Cap and wrap in aluminium foil for light protection.
5. Prepare a counter balance for the mill.
6. Mill for 4 hours, 20/s in a Retsch mill (for some substances up to 24 hours at 30/s).
7. Extract suspension from beads with two layers of filter (100 μm) on a filter holder, coupled to a recipient vial by centrifugation at 400 g for 2 min.
8. Move extract to measuring cylinder.
9. Repeat washing with small volumes(here 1 ml steps) until final volume is reached or extract is clear.
10. Fill up to final volume with gelatin and homogenize.

The above described preparation yields micro-suspensions of the compounds of formula I with particle sizes between 1 and 10 μm. The suspensions are suitable for oral applications and can be used in the in vivo assay described above.

Pharmaceutical compositions containing a compound of formula I or a pharmaceutically acceptable salt or ester thereof and a therapeutically inert carrier are also an object of the present invention, as is a process for their production, which comprises bringing one or more compounds of formula I and/or pharmaceutically acceptable salts or esters and, if desired, one or more other therapeutically valuable substances into a galenical administration form together with one or more therapeutically inert carriers.

In accordance with the invention compounds of formula I as well as their pharmaceutically acceptable salts or esters are useful in the control or prevention of illnesses. Based on their HER-signaling pathway inhibition and their antiproliferative activity, said compounds are useful for the treatment of diseases such as cancer in humans or animals and for the production of corresponding pharmaceutical compositions. The dosage depends on various factors such as manner of administration, species, age and/or individual state of health.

Consequently, the present invention also provides the following preferred embodiments:

(1) a process for the manufacture of the compounds of formula I or a salt or ester thereof
(2) a pharmaceutical composition, containing one or more compounds of formula I, together with pharmaceutically acceptable excipients;
(3) a pharmaceutical composition as defined above for the inhibition of tumor growth;
(4) the use of one or more compounds of formula I for the treatment of cancer;
(5) the use of one or more compounds of formula I for the manufacture of pharmaceutical compositions;
(6) the use of one or more compounds of formula I for the manufacture of corresponding pharmaceutical compositions for the inhibition of tumor growth.

The following examples and references are provided to aid the understanding of the present invention, the true scope of which is set forth in the appended claims. It is understood that modifications can be made in the procedures set forth without departing from the spirit of the invention.

EXAMPLE 1

4-[4-(4-Imidazol-1-yl-butyl)-phenoxymethyl]-2'-[2-(4-trifluoromethanesulfinyl-phenyl)-vinyl]-oxozole i) 1-(4-Bromo-butyl)-4-methoxy-benzene After starting the reaction by adding 5.00 ml 4-bromoanisole to a mixture of 4.86 g (0.20 mol) magnesium turnings and 100 ml THF, 20.00 ml 4-bromoanisole (total: 25.0 ml (37.4 g; 0.20 mol) were added at a pace sufficient to maintain reflux temperature. The reaction mixture was heated to reflux for additional 3 h, cooled to r.t. and dropped at 0° C. within 1 h to a stirred solution prepared by mixing 129.6 g (71.6 ml, 0.60 mol) 1,4-dibromo-butane in 200 ml THF with a freshly prepared solution of 0.17 g (4.0 mmol) LiCl and 0.267 g (2.0 mmol) Cu(II)Cl$_2$ in 20 ml THF. Stirring was continued for 12 h at r.t. followed by the addition of 100 ml of a 20% ammonium chloride solution and 200 ml ethyl acetate. The water phase was extracted twice with 50 ml ethyl acetate, all organic phases were combined, dried over sodium sulphate and evaporated. The resulting oil was fractionated by vacuum distillation. Yield: 27.7 g (57%), b.p. 112-115° C./0.15 mbar.

$^1$H-NMR(400 MHz, D$_6$-DMSO): δ=1.65(quintet, 2H, CH$_2$—CH$_2$-Ph), 1.77(quintet, 2H, CH$_2$—CH$_2$—Br), 2.53(t, 2H, CH$_2$-Ph), 3.53(t, 2H, CH$_2$—Br), 3.71(s, 3H, OCH$_3$), 6.84(d, 2H, 3-H/5-H), 7.10(d, 2H, 2-H/6-H).

ii) 1-[4-(4-Methoxy-phenyl)-butyl]-1H-imidazole

A mixture of 3.65 g (15.0 mmol) 1-(4-bromo-butyl)-4-methoxy-benzene, 1.02 g (15.0 mmol) imidazole, 2.74 g (16.5 mmol) potassium iodide, 0.60 g (15.0 mmol) sodium hydroxide and 20 ml 2-methyl-2-butanol was heated to reflux for 7 h. Solvents were distilled off, the residue dissolved in ethyl acetate and washed with water. Drying over Na$_2$SO$_4$ and removal of solvents in vacuo gave 2.0 g (58%) slightly coloured oil.

MS: M=231.2 (ESI+)
$^1$H-NMR(400 MHz, D$_6$-DMSO): δ=1.45(quintet, 2H, CH$_2$—CH$_2$—Ar), 1.68(quintet, 2H, CH$_2$—CH$_2$-imidazole), 2.51(t, 2H, CH$_2$—Ar), 3.71(s, 3H, OCH$_3$), 3.96(t, 2H, CH$_2$-imidazole), 6.83(d, 2H, 3'-/5'-H), 6.86(s, 1H, imidazole), 7.07 (d, 2H, 2'-/6'-H), 7.13(s, 1H, imidazole), 7.59(s, 1H, 2-H, imidazole).

iii) 4-(4-Imidazol-1-yl-butyl)-phenol 1.90 g (8.25 mmol) 1-[4-(4-methoxy-phenyl)-butyl]-1H-imidazole and 28 ml (247 mmol) 48% aqueous hydrobromic acid were stirred at 80° C. for 10 h. The mixture was cooled to 0° C., 23 ml of 4 N NaOH added, extracted with toluene and the aqueous phase adjusted to pH=6.3 by addition of 6 N HCl. The resulting precipitate was isolated, washed with ethyl acetate/n-heptane 2:1 and dried. 1.2 g (67%) slightly yellow powder.

MS: M=217.2 (ESI+)
$^1$H-NMR(400 MHz, D$_6$-DMSO): δ=1.42(quintet, 2H, CH$_2$—CH$_2$—Ar), 1.68(quintet, 2H, CH$_2$CH$_2$-imidazole), 2.50 (t, 2H, CH$_2$—Ar), 3.96(t, 2H, CH$_2$-imidazole), 6.65(d, 2H, 2H, 2'-/6'-H), 6.90(s, 1H, imidazole), 6.94(d, 2H, 3'-/5'-H), 7.16(s, 1H, imidazole), 7.66(s, 1H, 2-H, imidazole), 9.12(br, 1H, OH).

iv) 3-(4-Trifluoromethylsulfanyl-phenyl)-acrylic acid

A mixture of 5.42 g (26.3 mmol) 4-trifluoromethylsulfanyl-benzaldehyde, 3.12 g (30.0 mmol) malonic acid, 0.26 g (3.0 mmol) piperidine and 12.0 ml pyridine was kept at reflux temperature until carbon dioxide development ceased (5 h). The reaction mixture was poured into a solution of 50 ml ice water and 15 ml 6N HCl. The precipitate was isolated, washed with water, then with n-heptane and dried at 50° C. Yield: 5.9 g (85%) 3-(4-Trifluoromethylsulfanyl-phenyl)-acrylic acid.

MS: M=247.2 (API−)
$^1$H-NMR(400 MHz, D$_6$-DMSO): δ=6.65(d, 1H, 2-H), 7.63 (d, 1H, 3-H), 7.74(d, 2H, 3'-/5'-H), 7.84(d, 2H, 2'-/6'-H), 12.5(br, 1H, COOH).

v) 3-(4-Trifluoromethylsulfanyl-phenyl)-acrylamide

To a suspension of 5.24 g (21.1 mmol) 3-(4-trifluoromethylsulfanyl-phenyl)-acrylic acid in 30.0 ml tetrahydrofuran and 0.3 ml N,N-dimethyl formamide a solution of 2.75 ml (32.0 mmol) oxalyl chloride in 5.0 ml tetrahydrofuran was added dropwise at 0° C. within 20 min. Stirring was continued at 0-5° C. for 30 min. and 3 h at room temperature thereafter. The resulting solution was cooled to 0-5° C. again and then added within 15 min. to 100 ml of a 25% aqueous ammonia solution. After evaporation of the organic solvent, 200 ml water were added and the solution cooled. The precipitated amide was collected, washed with water and n-heptane and dried at 40° C. in vacuo. Yield 4.62 g (86%) 3-(4-trifluoromethylsulfanyl-phenyl)-acrylamide MS: M=248.1(API+)
$^1$H-NMR(400 MHz, D$_6$-DMSO): δ=6.72(d, 1H, 2-H), 7.21 (br, 1H, NH), 7.46(d, 1H, 3-H), 7.62(br, 1H, NH), 7.73(mc, 4H, Ar—H).

vi) 4-Chloromethyl-2-[2-(4-trifluoromethylsulfanyl-phenyl)-vinyl]-oxazole 4.45 g (18.0 mmol) 3-(4-trifluoromethylsulfanyl-phenyl)-acrylamide, 2.79 g (22.0 mmol) dichloro acetone and 50.0 ml toluene were kept at reflux temperature for 30 h with continuous removal of water by use of a Dean-Stark trap (a water separator used in chemical reactions). The reaction mixture was cooled for 30 min. in an ice bath and the precipitated amide (1.2 g) was removed by filtration and discarded. After removal of solvents in vacuo, the residue (5.92 g) was purified by chromatography on silica gel (eluent: heptane/ethyl acetate 1:1). All fractions containing the product were concentrated to a volume of 10 ml, n-heptane added and the crystallized material isolated by filtration, washed with cold heptane and dried. 2.02 g (35%) 4-Chloromethyl-2-[2-(4-trifluoromethylsulfanyl-phenyl)-vinyl]-oxazole.

MS: M=320.1(API+)

$^1$H-NMR(400 MHz, D$_6$-DMSO): δ=4.71(s, 2H, CH$_2$Cl), 7.30(d, 1H,=CH), 7.59(d, 1H, =CH), 7.74(d, 2H, Ar—H), 7.88(d, 2H, Ar—H), 8.21(s, 1H, oxazole).

vii) 4-Chloromethyl-2-[2-(4-trifluoromethanesulfinyl-phenyl)-vinyl]-oxazole

A mixture of 17.6 g (55 mmol) 4-chloromethyl-2-[2-(4-trifluoromethylsulfanyl-phenyl)-vinyl]-oxazole and 14.93 g (60 mmol) 3-chloro-benzenecarboperoxoic acid in 200 ml dichloromethane was stirred at room temperature over night. After filtration, the filtrate was washed three times with sodium hydroxide solution, then with water, dried over sodium sulfate, filtered and evaporated. Purification on silica, after elution with heptane/ethyl acetate 5:1, yielded 5.78 g (31%) 4-chloromethyl-2-[2-(4-trifluoromethanesulfinyl-phenyl)-vinyl]-oxazole as off-white solid melting at 102-104° C.

$^1$H-NMR(400 MHz, D$_6$-DMSO): δ=4.72(s, 2H, ClCH$_2$), 7.38(d, 1H, vinyl-H), 7.65 (d, 1H, vinyl-H), 7.92(d, 2H, Ar—H), 8.07(d, 2H, Ar—H), 8.23(s, 1H, oxazole).

viii) 4-[4-(4-Imidazol-1-yl-butyl)-phenoxymethyl]-2-[2-(4-trifluoromethane-sulfinyl-phenyl)-vinyl]-oxazole 13.0 mg (0.50 mmol) 95% sodium hydride were given to a solution of 108 mg (0.50 mmol) 4-(4-Imidazol-1-yl-butyl)-phenol in 4.0 ml DMF and stirred for 15 min. 168 mg (0.50 mmol) 4-chloromethyl-2-[2-(4-trifluoromethanesulfinyl-phenyl)-vinyl]-oxazole were added and stirring continued overnight. After addition of 10 ml water the resulting precipitate was washed with water, 10 ml methanol/water 1:1 and with diethyl ether. The residue was purified by chromatography on silica gel (eluent: ethyl acetate/methanol 9:1) to yield 167 mg colorless powder that was further purified by HPLC-MS to give 75 mg (29%) colorless powder.

MS: M=516.1 (ESI+)

$^1$H-NMR(400 MHz, CDCl$_3$)δ=1.59(quintet, 2H, CH$_2$—CH$_2$—Ar), 1.80(quintet, 2H, CH$_2$-CH$_2$-imidazole), 2.58(t, 2H, CH$_2$—Ar), 3.93(t, 2H, CH$_2$-imidazole), 5.03(s, 2H, OCH$_2$), 6.92(d, 3H, 3'-/5'-H—Ar; 1H, imidazole), 7.07 (m, 4H; 2H, 2'-/6'-H—Ar; 1H, 1H, imidazole), 7.47(s, 1H, 2-H, imidazole), 7.57(d, 1H, vinyl-H), 7.70(s, 1H, oxazole), 7.74(d, 2H, ArSOCF$_3$), 7.82(d, 2H, ArSOCF$_3$).

EXAMPLE 2

2-{1-[4-(4-{2-[(E)-2-(-4-Trifluoromethanesulfinyl-phenyl)-vinyl]-oxazol-4-ylmethoxy}-phenyl)-butyl]-1H-imidazol-2-yl}-ethanol i) 2-{1-[4-(4-Methoxy-phenyl)-butyl]-1H-imidazol-2-yl}-ethanol A mixture of 3.65 g (15.0 mmol) 1-(4-bromo-butyl)-4-methoxy-benzene, 2.52 g (22.5 mmol) 2-(1H-imidazol-2-yl)-ethanol, 2.74 g (16.5 mmol) potassium iodide, 0.90 g (22.5 mmol) sodium hydroxide and 15 ml 2-methyl-2-butanol was heated to reflux for 12 h. Solvents were distilled off, the residue dissolved in toluene and washed with water. After drying over Na$_2$SO$_4$ and removal of solvents in vacuo the residue was stirred with 7 ml ethyl acetate, isolated by filtration, washed with ethyl acetate and dried. Yield 2.41 g (59%).

MS: M=275.4 (ESI+).

ii) 4-{4-[2-(2-Hydroxyethyl)-imidazol-1-yl]-butyl}-phenol 2.40 g (8.75 mmol) 2-{1-[4-(4-methoxy-phenyl)-butyl]-1H-imidazol-2-yl}-ethanol and 9 ml (81 mmol) 48% aqueous hydrobromic acid were stirred at 80° C. for 12 h. The mixture was cooled to 0° C., 23 ml 4 N NaOH added, extracted with toluene and the aqueous phase adjusted to pH=6.3 by addition of 1 N HCl. The resulting precipitate was isolated, washed twice with water and ethyl acetate and dried. 1.71 g (75%) yellow crystals.

$^1$H-NMR(400 MHz, D$_6$-DMSO): δ=1.47(quintet, 2H, CH$_2$—CH$_2$—Ar), 1.64(quintet, 2H, CH$_2$-CH$_2$-imidazole), 2.48(t, 2H, CH$_2$—Ar), 2.73(t, 2H, CH$_2$—CH$_2$OH), 3.68(q, 2H, CH$_2$OH), 3.88(t, 2H, CH$_2$-imidazole), 4.76(t, 1H, CH$_2$OH), 6.65(d, 2H, 2'-/6'-H), 6.74(s, 1H, imidazole), 6.95(d, 2H, 3'-/5'-H), 7.00(s, 1H, imidazole), 9.12(br, 1H, PhOH).

iii) 2-{1-[4-(4-{2-[(E)-2-(-4-Trifluoromethanesulfinyl-phenyl)-vinyl]-oxazol-4-ylmethoxy}-phenyl)-butyl]-1H-imidazol-2-yl}-ethanol 13.0 mg (0.50 mmol) 95% sodium hydride were given to a solution of 130 mg (0.50 mmol) 4-{4-[2-(2-Hydroxyethyl)-imidazol-1-yl]-butyl}-phenol in 4.0 ml DMF and stirred for 15 min. 168 mg (0.50 mmol) 4-chloromethyl-2-[2-(4-trifluoromethanesulfinyl-phenyl)-vinyl]-oxazole were added and stirring continued at r.t. overnight. After addition of 10 ml water the resulting precipitate was washed twice with water, 10 ml methanol/water 1:1 and with diethyl ether. The residue was purified by chromatography on silica gel (eluent: ethyl acetate/methanol 9:1) to yield 99 mg colorless powder that was further purified by HPLC-MS.

MS: M=560.2 (ESI+)

$^1$H-NMR(400 MHz, CDCl$_3$): δ=1.61(quintet, 2H, CH$_2$—CH$_2$—Ar), 1.73(quintet, 2H, CH$_2$-CH$_2$-imidazole), 2.61(t, 2H, CH$_2$—Ar), 2.82(t, 2H, CH$_2$—CH$_2$OH), 3.84(q, 2H, CH$_2$OH), 4.03(t, 2H, CH$_2$-imidazole), 5.03(s, 2H, OCH$_2$), 6.80(s, 1H, imidazole), 6.95(d, 3H, 3'-/5'-1H, imidazole), 7.08(m, 3H; 2H, 2'-/6'-H—Ar; 1H, vinyl-H), 7.60(d, 1H, vinyl-H), 7.77(s, 1H, oxazole), 7.78(d, 2H, ArSOCF$_3$), 7.87(d, 2H, ArSOCF$_3$).

EXAMPLE 3

(2-[1,2,3]Triazol-1-yl-ethyl)-(4-{2-[(E)-2-(4-trifluoromethanesulfinyl-phenyl)-vinyl]-oxazol-4-ylmethoxy}-benzyl)-amine i) 4-{2-[(E)-2-(4-trifluoromethanesulfinyl-phenyl)-vinyl]-oxazol-4-ylmethoxy}-benzaldehyde A suspension of 250 mg (0.74 mmol) 4-chloromethyl-2-[2-(4-trifluoromethanesulfinyl-phenyl)-vinyl]-oxazole, 90 mg (0.74 mmol) 4-hydroxy-benzaldehyde, 147 mg (0.45 mmol) cesium carbonate and 123 mg (0.74 mmol) potassium iodide in 25 ml butanone was stirred at 60° C. over night. After evaporation, the residue was quenched with water and extracted with ethyl acetate. The extract was washed with sodium hydroxide solution and water, dried, concentrated and purified on silica. Elution with heptane/ethyl acetate 5:1 containing 1% acetic acid yielded 245 mg (78%) 4-{2-[(E)-2-(4-trifluoromethanesulfinyl-phenyl)-vinyl]-oxazol-4-ylmethoxy}-benzaldehyde as white crystals, melting at 144-147° C.

MS: M=422.0(ESI+)

$^1$H-NMR(400 MHz, D$_6$-DMSO): δ=5.19(s, 2H, CH$_2$), 7.26(d, 2H, Ar—H), 7.39(d, 1H, vinyl-H), 7.65(d, 1H, vinyl-H), 7.91(2d, 4H, Ar—H), 8.06(d, 2H, Ar—H), 8.32(s, 1H, oxazole), 9.89(s, 1H, formyl).

ii) (2-[1,2,3] Triazol-1-yl-ethyl)-(4-{2-[(E)-2-(4-trifluoromethanesulfinyl-phenyl)-vinyl]-oxazol-4ylmethoxy}-benzyl)-amine A solution of 120 mg (0.28 mmol) 4-{2-[(E)-2-(4-trifluoromethanesulfinyl-phenyl)-vinyl]-oxazol-4-ylmethoxy}-benzaldehyde, 31 mg (0.28 mmol) (2-[1,2,3]triazol-1-yl-ethyl)-amine and 5 mg toluene-4-sulfonic acid in 10 ml methanol was stirred at room temperature for 1 hour, then 18 mg (0.28 mmol) sodium cyanoborohydride was added and the mixture stirred over night. After evaporation and chromatography on silica with ethyl acetate/methanolic ammonia 85:15, the title compound was isolated as light yellow solid melting at 111-113° C.; yield 89 mg (60%).

MS: M=518.3(ESI+)

$^1$H-NMR(400 MHz, D$_6$-DMSO): δ=2.18(br, 1H, NH), 2.90(t, 2H, CH$_2$), 3.62(s, 2H, NCH$_2$), 4.44(t, 2H, CH$_2$), 5.01 (s, 2H, OCH$_2$), 6.97(d, 2H, Ar—H), 7.20(d, 2H, Ar—H), 7.38(d, 1H, =CH), 7.64(d, 1H,=CH), 7.70(s, 1H, triazole), 7.91(d, 2H, Ar—H), 8.06(d, 2H, Ar—H), 8.10(s, 1H, triazole), 8.25(s, 1H, oxazole).

EXAMPLE 4

1-[4-(4-{2-[(E)-2-(-4-Trifluoromethanesulfinyl-phenyl)-vinyl]-oxazol-4-ylmethoxy}-phenyl)-butyl]-1H-[1,2,3]triazole A mixture of 0.815 g (3.75 mmol) 4-(4-[1,2,3]triazol-1-yl-butyl)-phenol and 0.815 g (2.50 mmol) cesium carbonate in 15 ml butanone was stirred at 60° C. for 30 min, then 1.40 g (4.17 mmol) 4-chloromethyl-2-[2-(4-trifluoromethanesulfinyl-phenyl)-vinyl]-oxazole and 0.692 g (4.17 mmol) potassium iodide were added and stirring at 60° C. continued for 40 hours. After evaporation, 50 ml water was added and the mixture extracted with two portions of 50 ml ethyl acetate. The combined organic layers were washed with 1N sodium hydroxide and water, dried over sodium sulfate and evaporated to give 2.20 g raw product. After chromatography on silica, eluent dichloromethane/methanol 20:1, resulted 1.40 g (72%) pure title compound as tan crystals melting at 122-123° C.

MS: M=517.2(ESI+)

$^1$H-NMR(400 MHz, CDCl$_3$), δ=1.61(q, 2H, CH$_2$), 1.94(q, 2H, CH$_2$), 2.60(t, 2H, CH$_2$), 4.39(t, 2H, CH$_2$), 5.02(s, 2H, CH$_2$), 6.91(d, 2H, Ar—H), 7.05(d, 2H, Ar—H), 7.06(d, 1H, vinyl), 7.50(s, 1H, triazole), 7.57(d, 1H, vinyl), 7.69(s, 1H, triazole), 7.70(s, 1H, oxazole), 7.74(d, 2H, Ar—H), 7.82(d, 2H, Ar—H).

Alternative preparation of

1-[4-(4-{2-[(E)-2-(-4-Trifluoromethanesulfinyl-phenyl)-vinyl]-oxazol-4-ylmethoxy}-phenyl)-butyl]-1H-[1,2,3]triazole To a solution of 200 mg (0.4 mmol) 1-[4-(4-{2-[(E)-2-(-4-trifluoromethane-sulfanyl-phenyl)-vinyl]-oxazol-4-ylmethoxy}-phenyl)-butyl]-1H-[1,2,3]triazole in 15 ml dichloromethane was added 99 mg (0.44 mmol) 3-chloro-benzenecarboperoxoic acid and the mixture stirred for two days at room temperature. Another 50 mg (0.22 mmol) 3-chloro-benzenecarboperoxoic acid was added and stirring continued over night. After addition of 20 ml dichloromethane, the solution was washed with sodium carbonate solution and water, dried, evaporated and purified on silica. Elution with ethyl acetate/heptane 3:1 afforded 63 mg (30%) title compound melting at 120-122° C.

EXAMPLE 5

1-[4-(4-{2-[(E)-2-(-4-Trifluoromethanesulfonyl-phenyl)-vinyl]-oxazol-4-ylmethoxy}-phenyl)-butyl]-1H-[1,2,3]triazole To a solution of 100 mg (0.2 mmol) 1-[4-(4-{2-[(E)-2-(-4-trifluoromethylsulfanyl-phenyl)-vinyl]-oxazol-4-ylmethoxy}-phenyl)-butyl]-1H-[1,2,3]triazole in 50 ml chloroform was added 134 mg (0.60 mmol) 3-chloro-benzenecarboperoxoic acid and the mixture stirred for two days at room temperature. Another 67 mg (0.30 mmol) 3-chloro-benzenecarboperoxoic acid was added and stirring continued for three days. After addition of 30 ml dichloromethane, the solution was washed with sodium carbonate solution and water, dried, evaporated and purified on reversed phase (C4). Elution with methanol/water 20 to 80% containing 0.1% formic acid afforded 50 mg (47%) title compound melting at 133-135° C.

MS: M=533.4(ESI+)

$^1$H-NMR(400 MHz, DMSO-D$_6$); δ=1.24(q, 2H, CH$_2$), 1.81(q, 2H, CH$_2$), 3.32(t, 2H, CH$_2$), 4.39(t, 2H, CH$_2$), 5.00(s, 2H, CH$_2$), 6.96(d, 2H, Ar—H), 7.09(d, 2H, Ar—H), 7.51(d, 1H, vinyl), 7.68(s, 1H, triazole), 7.71(s, 1H, triazole), 8.13(d, 1H, vinyl), 8.16(m, 4H, Ar—H), 8.29(s, 1H, oxazole).

EXAMPLE 6

4-[4-(4-{2-[(E)-2-(-4-Trifluoromethanesulfinyl-phenyl)-vinyl]-oxazol-4-ylmethoxy}-phenyl)-butyl]-1H-[1,2,3]triazole i) 1-(4-Iodo-butyl)-4-methoxy-benzene A mixture consisting of 30.2 g (124 mmol) 1-(4-bromo-butyl)-4-methoxy-benzene, 19.2 g (128 mmol) sodium iodide and 508 ml acetone was heated to reflux temperature for 1 h. The resulting suspension was cooled to r.t. and the precipitated sodium bromide removed by filtration. The filtrate was stripped off the solvents by vacuum distillation and the residue distributed between water and diethyl ether. After drying of the organic phase over sodium sulphate, vacuum distillation gave 34.9 g (97%) of the title compound as slightly yellow liquid.

MS: M=290.0 (EI).

ii) [6-(4-Methoxy-phenyl)-hex-1-ynyl]-trimethyl-silane b 12.4 ml (19.8 mmol) Of 1.6 M butyllithium in n-hexane was added dropwise at −78° C. to a solution of 1.94 g (2.80 ml, 19.8 mmol) trimethylsilylacetylene and 2.39 ml (19.8 mmol) DMPU in 30 ml THF. After stirring for 1 h at −78° C. a solution of 28.7 g (9.89 mmol) 1-(4-Iodo-butyl)-4-methoxy-benzene in 30 ml THF was added at −78° C. and stirring continued for 30 min. The reaction mixture was allowed to warm to r.t. overnight and then hydrolyzed by a saturated ammonium chloride solution. The water phase was extracted with ether and the combined organic phases were dried over sodium sulphate. Removal of solvents in vacuo gave 3.20 g yellow liquid, which still contained solvent and was used without further purification.

MS: M=260.1 (EI).

$^1$H-NMR(400 MHz, CDCl$_3$); δ=0.15(s, 9H, Si(CH$_3$)$_3$), 1.57(quintet, 2H, CH$_2$—CH$_2$—C≡C), 1.70(quintet, 2H, CH$_2$—CH$_2$—Ar), 2.19(t, 2H, CH$_2$—C≡C), 2.59(t, 2H, CH$_2$—Ar), 3.78(s, 3H, OCH$_3$), 6.81(d, 2H, 3'-/5'-H), 7.08(d, 2H, 2'-H/6'-H).

iii) 1-Hex-5-ynyl-4-methoxy-benzene

A mixture of 3.20 g (12.3 mmol) [6-(4-methoxy-phenyl)-hex-1-ynyl]-trimethyl-silane, 50 ml methanol and 12.3 ml (24.6 mmol) 2N NaOH was stirred for 2 h at r.t. After neutralization with 13 ml 2N HCl methanol was distilled off and the aqueous phase extracted with diethyl ether. Drying ($Na_2SO_4$) and removal of solvents in vacuo gave 1.80 g (78%) of the title compound.

MS: M=188.1 (ESI).

$^1$H-NMR(400 MHz, $CDCl_3$); δ=1.55(quintet, 2H, $CH_2$—$CH_2$—C≡C), 1.69(quintet, 2H, $CH_2$-$CH_2$—Ar), 1.94(t, 1H, C≡CH), 2.26(dt, 2H, $CH_2$—C≡CH), 2.60(t, 2H, $CH_2$—Ar), 3.78(s, 3H, $OCH_3$), 6.83(d, 2H, 3'-/5'-H), 7.09(d, 2H, 2'-H/6'-H).

iv) 4-(4-(4-Methoxy-phenyl)-butyl)-1H-[1,2,3]triazole

A mixture of 1.80 g (9.56 mmol) 1-hex-5-ynyl-4-methoxy-benzene, 1.86 g (28.6 mmol) sodium azide, 1.53 g (28.6 mmol) ammonium chloride and 80 ml DMF was kept at 125° C. for 7 d with an extra addition of 1.80 g sodium azide and 1.53 g ammonium chloride every day. After cooling to r.t. the dark reaction mixture was distributed between water and ethyl acetate. The organic phase was dried over sodium sulphate and the solvent distilled off. The residue was separated by HPLC on a RP18-endcapped column (methanol/water) (a reversed phase column PUROSPHER® STAR RP-18 endcapped from Merk KGaA, Darmstadt, Germany, which is used with methanol/water as eluent) to yield 450 mg 5-(4-(4-Methoxy-phenyl)-butyl)-2H-tetrazole and 500 mg 4-(4-(4-Methoxy-phenyl)-butyl)-1H-[1,2,3]triazole.

5-(4-(4-Methoxy-phenyl)-butyl)-2H-tetrazole:

MS: M=233.3(APCI+), 231.3(APCI−).

$^1$H-NMR(400 MHz, $CDCl_3$); δ=1.67(quintet, 2H, $CH_2$—$CH_2$—Ar), 1.87(quintet, 2H, $CH_2$-$CH_2$-tetrazole), 2.56 (t, 2H, $CH_2$—Ar), 3.08(t, 2H, $CH_2$-tetrazole), 3.74(s, 3H, $OCH_3$), 6.76(d, 2H, 3'-/5'-H), 6.97(d, 2H, 2'-/6'-H), 11.5-12.5 (br, 1H, NH).

4-(4-(4-Methoxy-phenyl)-butyl)-1H-[1,2,3]triazole:

MS: M=232.2(APCI+), 230.2(APCI—).

$^1$H-NMR(400 MHz, $D_6$-DMSO): δ=1.50-1.65(m, 4H), 2.53(t, 2H, $CH_2$—Ar), 2.65(t, 2H, $CH_2$-triazole), 3.71(s, 3H, $OCH_3$), 6.83(d, 2H, 3'-/5'-H), 7.08(d, 2H, 2'-/6'-H), 7.5(br, 1H, 5-H-triazole), 14-15(br, 1H, NH).

v) 4-(4-1H-[1,2,3]triazol-4-yl-butyl)-phenol

A mixture of 500 mg 4-(4-(4-methoxy-phenyl)-butyl)-1H-[1,2,3]triazole and 1.5 ml 48% hydrobromic acid was stirred at 80° C. for 9 h. After adjustment to pH=6 by addition of conc. sodium hydroxide solution, the aqueous layer was discarded and the remaining sticky residue purified by HPLC-MS(RP18, methanol/water 7:3, pH=2.3). Yield 170 mg (36%).

MS: M=218.2(APCI+), 216.2(APCI−).

$^1$H-NMR(400 MHz, $D_6$-DMSO): δ=1.55(mc, 4H, $CH_2$), 2.48(t, 2H, $CH_2$—Ar), 2.64(t, 2H, $CH_2$-triazole), 6.65(d, 2H, 2'-/6'-H), 6.95(d, 2H, 3'-/5'-H), 7.58(br, 1H, 5-H-triazole), 9.08(br, 1H, NH).

vi) 4-[4-(1-Trityl-1H-[1,2,3]triazol-4-yl)-butyl]-phenol

A solution of 706 mg (5.06 mmol) triphenylchloromethane in 5.0 ml DMF was added at 0° C. to a solution of 500 mg (2.30 mmol) 4-(4-1H-[1,2,3]triazol-4-yl-butyl)-phenol and 512 mg (5.06 mmol) triethylamine in 5.0 ml DMF. The mixture was allowed to reach r.t. overnight and solvents were removed in vacuo. After distribution of the residue between water and ethyl acetate, the organic phase was dried (sodium sulphate), solvents distilled off and the residue purified by column chromatography on silica gel (heptane/ethyl acetate 2:1).

Yield 610 mg (58%).

MS: M=460.2(ESI+), 482.2 (ESI+, M+$Na^+$), 458.2 (ESI−).

$^1$H-NMR(400 MHz, $CDCl_3$); δ=1.59(mc, 2H, $CH_2$—$CH_2$—Ar), 1.67(mc, 2H, $CH_2$—$CH_2$-triazole), 2.53(t, 2H, $CH_2$—Ar), 2.71(t, 2H, $CH_2$-triazole), 5.10(s, 1H, OH), 6.72(d, 2H, 2'-/6'-H), 6.97(d, 2H, 3'-/5'-H), 7.05-7.40(m, 15H, trityl).

vii) 4-[4-(4-{2-[(E)-2-(-4-Trifluoromethanesulfinyl-phenyl)-vinyl]-oxazol-4-ylmethoxy}-phenyl)-butyl]-1-trityl-1H-[1,2,3]triazole 8.1 mg (0.20 mmol) 95% sodium hydride were given at 0° C. to a solution of 90 mg (0.20 mmol) 4-[4-(1-trityl-1H-[1,2,3]triazol-4-yl)-butyl]-phenol in 3.0 ml N,N-dimethylformamide and stirred for 15 min. 66 mg (0.20 mmol) 4-chloromethyl-2-[2-(4-trifluoromethanesulfinyl-phenyl)-vinyl]-oxazole were added and stirring continued at 25° C. for 2 h. The reaction mixture was poured into water and extracted with ethyl acetate. The organic phase was dried over sodium sulphate and the solvents distilled off in vacuo. Yield 146 mg.

MS: M=781.41(APCI+, M+$Na^+$).

viii) 4-[4-(4-{2-[(E)-2-(-4-Trifluoromethanesulfinyl-phenyl)-vinyl]-oxazol-4-ylmethoxy}-phenyl)-butyl]-1H-[1,2,3]triazole A mixture of 146 mg (0.192 mmol) 4-[4-(4-{2-[(E)-2-(-4-trifluoromethanesulfinyl-phenyl)-vinyl]-oxazol-4-yl-methoxy}-phenyl)-butyl]-1-trityl-1H-[1,2,3]triazole, 300 μl formic acid, 10 μl water and 6 ml tetrahydrofuran was stirred at 60° C. for 24 h. After removal of solvents in vacuo 4-[4-(4-{2-[(E)-2-(4-trifluoromethane-sulfinyl-phenyl)-vinyl]-oxazol-4-ylmethoxy}-phenyl)-butyl]-1H-[1,2,3]triazole was obtained by HPLC-MS-purification.

MS: M=517.0(APCI+), 515.0(APCI−).

$^1$H-NMR(400 MHz, $D_6$-DMSO): main tautomer, δ=1.58 (m, 4H), 2.54(t, 2H, $CH_2$—Ar), 2.65(t, 2H, $CH_2$-triazole), 4.99(s, 2H, $OCH_2$), 6.94(d, 2H, 3'-/5'-H), 7.11(d, 2H, 2'-/6'-H), 7.38(d, 1H, vinyl-H), 7.5(br, 1H, triazole), 7.67(d, 1H, vinyl-H), 7.92(d, 2H, $ArSOCF_3$), 8.04(d, 2H, $ArSOCF_3$), 8.25(s, 1H, oxazole), 14-15(br, 1H, NH).

EXAMPLE 7

5-[4-(4-{2-[(E)-2-(-4-Trifluoromethanesulfinyl-phenyl)-vinyl]-oxazol-4-ylmethoxy}-phenyl)-butyl]-2H-tetrazole i) 4-(4-2H-tetrazol-5-yl-butyl)-phenol 450 mg (1.94 mmol) 5-(4-(4-methoxy-phenyl)-butyl)-2H-tetrazole and 1.5 ml 48% aqueous hydrobromic acid were stirred at 80° C. for 17 h. The reaction mixture was adjusted to pH=4 by addition of conc. NaOH and the aqueous phase discarded. Purification of the undissolved residue by HPLC-MS (methanol/water 7:3, pH=2.3) gave 220 mg (52%) of the title compound.

MS: M=219.3(APCI+), 217.3(APCI−).

$^1$H-NMR(400 MHz, $D_6$-DMSO): δ=1.53(quintet, 2H, $CH_2$—$CH_2$—Ar), 1.68(quintet, 2H, $CH_2$-$CH_2$-tetrazole), 2.48 (t, 2H, $CH_2$—Ar), 2.89(t, 2H, $CH_2$-tetrazole), 6.65(d, 2H, 2'-/6'-H), 6.96(d, 2H, 3'-/5'-H), 9.1(br, 1H, OH), 16(br, 1H, NH).

ii) 5-[4-(4-{2-[(E)-2-(-4-Trifluoromethanesulfinyl-phenyl)-vinyl]-oxazol-4-ylmethoxy}-phenyl)-butyl]-2H-tetrazole 47.5 mg (1.88 mmol) 95% sodium hydride were given at 0° C. to a solution of 200 mg (0.916 mmol) 4-(4-2H-tetrazol-5-yl-butyl)-phenol in 5.0 ml N,N-dimethylformamide and stirred for 15 min. 308 mg (0.916 mmol) 4-chloromethyl-2-[2-(4-trifluoromethanesulfinyl-phenyl)-vinyl]-oxazole were added and stirring continued at 25° C. for 2 h. The reaction mixture was neutralized with HCl, poured into water and the resulting precipitate washed with little methanol and diethyl ether. The obtained material (180 mg) was purified by chromatography on silica gel (dichloromethane/methanol 100:4) to give 80 mg of the title compound.

MS: M=518.0 (APCI+), 516.0 (APCI−).

$^1$H-NMR(400 MHz, D$_6$-DMSO): δ=1.57(quintet, 2H, C$\underline{H}_2$—CH$_2$—Ar), 1.70(quintet, 2H, C$\underline{H}_2$-CH$_2$-tetrazole), 2.53 (t, 2H, CH$_2$—Ar), 2.89(t, 2H, CH$_2$-tetrazole), 4.99(s, 2H, OCH$_3$), 6.95(d, 2H, 2'-/6'-H), 7.11(d, 2H, 3'-/5'-H), 7.38(d, 1H, vinyl-H), 7.64(d, 1H, vinyl-H), 7.91(d, 2H, ArSOCF$_3$), 8.06(d, 2H, ArSOCF$_3$), 8.25(s, 1H, oxazole), 16(br, 1H, NH).

EXAMPLE 8

1-[2-(4-{2-[-4-(Trifluoromethanesulfinyl-phenyl)-vinyl]-oxazol-4-ylmethoxy}-benzyloxy)-ethyl]-1H-[1,2,3]-triazole i) 1-Allyloxy-4-chloromethyl-benzene 7.67 g (67.0 mmol) methanesulfonyl chloride were given at 0° C. to a solution of 10.0 g (60.9 mmol) (4-allyloxy-phenyl)-methanol and 9.34 ml (67.0 mmol) triethylamine in 35 ml dichloromethane and stirred at r.t. overnight. The mixture was poured in ice water, extracted with dichloromethane and the organic phase dried over Na$_2$SO$_4$. After removal of solvents the residue was purified by chromatography on silica gel (ethyl acetate/n-heptane 1:5) to yield 3.12 g (28%) pale yellow oil.

$^1$H-NMR(400 MHz, D$_6$-DMSO): δ=4.57(m, 2H, OCH$_2$), 4.72(s, 2H, CH$_2$Cl), 5.26(d, 1H, =CH$_2$), 5.39(d, 1H,=CH$_2$), 6.04(m, 1H, CH=CH$_2$), 6.95(d, 2H, 2'-/6'-H), 7.35(d, 2H, 3'-/5'-H).

ii) 1-[2-(4-Allyloxy-benzyloxy)-ethyl]-1H-[1,2,3]-triazole 197 mg 8.21 mmol) 95% sodium hydride were given at −50° C. to a solution of 1.00 g (5.47 mmol) 1-allyloxy-4-chloromethyl-benzene and 619 mg (5.47 mmol) 2-(1H-[1,2,3]-triazol-1-yl)-ethanol in 9.0 ml DMF. The mixture was allowed to warm slowly to r.t., stirred overnight and 10 ml water added. The formed oil was collected with 10 ml dichloromethane, the aqueous phase extracted with 10 ml dichloromethane and the combined organic phases dried over Na$_2$SO$_4$.

Solvents were removed in vacuum and the residue purified by chromatography on silica gel (ethyl acetate/heptane 1:1) to yield 1.10 g (78%) yellow oil. MS: M=260.3 (APCI+), 258.3 (APCI−).

$^1$H-NMR(400 MHz, D$_6$-DMSO): δ=3.79(t, 2H, C$\underline{H}_2$—CH$_2$-triazole), 4.39(s, 2H, OCH$_2$PH), 4.54-4.59(m, 4H, OCH$_2$-vinyl, CH$_2$-triazole), 5.25(d, 1H,=CH$_2$), 5.38(d, 1H,=CH$_2$), 6.06(m, 1H, CH=CH$_2$), 6.89(d, 2H, 2'-/6'-H), 7.15(d, 2H, 3'-/5'-H), 7.16(s, 1H, triazole), 8.08(s, 1H, triazole).

iii) 4-(2-[1,2,3]Triazol-1-yl-ethoxymethyl)-phenol

A solution of 500 mg (1.93 mmol) 1-[2-(4-allyloxy-benzyloxy)-ethyl]-1H-[1,2,3]-triazole in 10 ml dichloromethane was added to a solution of 904 mg (5.79 mmol) 1,3-dimethylbarbituric acid and 58 mg (0.05 mmol) Pd(PPh$_3$)$_4$ in 20 ml dichloromethane and stirred for 4.5 h at 40° C. The mixture was extracted with 3×20 ml sat. NaHCO$_3$-solution and 8 ml water and the combined aqueous phases were reextracted with 2×10 ml dichloromethane. The organic extracts were combined and dried over MgSO$_4$. Solvents were distilled off and the residue purified by chromatography on silica gel (ethyl acetate) to yield 248 mg (59%) of the title compound.

$^1$H-NMR(400 MHz, D$_6$-DMSO): δ=3.77(t, 2H, C$\underline{H}_2$—CH$_2$-triazole), 4.33(s, 2H, OCH$_2$PH), 4.56(t, 2H, CH$_2$-triazole), 6.69(d, 2H, 2'-/6'-H), 7.03(d, 2H, 3'-/5'-H), 7.11(s, 1H, triazole), 8.07(s, 1H, triazole), 9.37(s, 1H, PhOH).

iv) 1-[2-(4-{2-[(E)-2-(-4-Trifluoromethanesulfinyl-phenyl)-vinyl]-oxazol-4-ylmethoxy}-phenyl- methoxy)-ethyl]-1H-[1,2,3]triazole 13.0 mg (0.50 mmol) 95% sodium hydride were given to a solution of 110 mg (0.50 mmol) 4-(2-[1,2,3]triazol-1-yl-ethoxymethyl)-phenol in 4.0 ml DMF and stirred for 15 min. 168 mg (0.50 mmol) 4-chloromethyl-2-[2-(4-trifluoromethanesulfinyl-phenyl)-vinyl]-oxazole were added and stirring continued at r.t. overnight. After addition of 10 ml water the resulting precipitate was washed twice with 10 ml water, 2×10 ml methanol/water 1:1 and with diethyl ether. The residue was purified by chromatography on silica gel (eluent: ethyl acetate/n-heptane 3:1) to yield 80 mg (31%) colorless powder.

MS: M=519.2 (ESI+)

$^1$H-NMR(400 MHz, D$_6$-DMSO): δ=3.80(t, 2H, CH$_2$—CH$_2$-triazole), 4.40(s, 2H, OCH$_2$-ph), 4.58(t, 2H, CH$_2$-triazole), 5.02(s, 2H, OCH$_2$-oxazole), 6.99(d, 2H, 3'-/5'-H—Ar), 7.18(d, 2H; 2H, 2'-/6'-H—Ar) 7.38(d, 1H, vinyl-H), 7.64(d, 1H, vinyl-H), 7.72(s, 1H, triazole), 7.19(d, 2H, ArSOCF$_3$), 8.06(d, 2H, ArSOCF$_3$), 8.08(s, 1H, triazole), 8.29(s, 1H, oxazole).

EXAMPLE 9

1-[2-(4-{2-[(E)-2-(4-Trifluoromethanesulfinyl-phenyl)-vinyl]-oxazol-4-ylmethoxy}-phenylmethanesulfinyl)-ethyl]-1H-[1,2,3]triazole i) (4-Allyloxy-phenyl)-methanethiol A mixture of 2.00 g (10.9 mmol) 1-allyloxy-4-chloromethyl-benzene and 917 mg (12.1 mmol) thiourea in 3.0 ml ethanol was heated to reflux for 7 h. Solvents were distilled off and the crystalline residue was washed with cold ethanol and isolated by filtration. After addition of 2.5 ml ethanol, 1.0 ml water and 0.7 ml 25% aqueous ammonia, the mixture was heated to reflux for 1 h. Ethanol was distilled off, then acidified with 0.5 ml half conc. HCl and extracted with ethyl acetate. The solution was dried over MgSO$_4$ and solvents were removed in vacuo to yield 1.59 g (81%) colorless oil, which was used immediately.

$^1$H-NMR(400 MHz, D$_6$-DMSO): δ=2.75(s, 1H, SH), 3.68 (s, 2H, CH$_2$SH), 4.54(m, 2H, OCH$_2$-vinyl), 5.26(d, 1H,=CH$_2$), 5.38(d, 1H,=CH$_2$), 6.05(m, 1H, CH=CH$_2$), 6.89 (d, 2H, 2'-/6'-H), 7.24(d, 2H, 3'-/5'-H).

ii) Toluene-4-sulfonic acid 2-[1,2,3]triazol-1-yl-ethyl ester

A solution of 12.9 g (66.3 mmol) p-toluenesulfonic acid chloride, 2.03 g (16.6 mmol) 4-(N,N-dimethylamino)-pyridine and 11.2 ml (80.2 mmol) triethylamine in 150 ml dichloromethane was cooled to -10° C. A solution of 7.50 g (66.3 mmol) 2-(1H-[1,2,3]-triazol-1-yl)-ethanol in 150 ml dichloromethane was added dropwise and the mixture stirred overnight at -4° C. 170 ml Ice and 170 ml dichloromethane were added and stirring continued for 10 min. followed by addition of 3.9 ml conc. HCl. The organic phase was separated, washed with sat. NaHCO$_3$-solution and brine, dried over Na$_2$SO$_4$ and solvents distilled off. Yield 15.3 g (86%) orange crystals.

$^1$H-NMR(400 MHz, D$_6$-DMSO): δ=2.41(s, 3H, CH3), 4.41(t, 2H, CH$_2$-OTos), 4.67(t, 2H, CH$_2$-triazole), 7.44(d, 2H, Ar—H), 7.65(d, 2H, Ar—H), 7.69(s, 1H, triazole), 8.03 (s, 1H, triazole).

iii) 1-[2-(4-Allyloxy-benzylsulfanyl)-ethyl]-1H-[1,2,3]triazole 1.58 g (6.14 mmol) (4-allyloxy-phenyl)-methanethiol and 1.64 g (6.14 mmol) toluene-4-sulfonic acid 2-[1,2,3]triazol-1-yl-ethyl ester were dissolved in 15 ml DMF and cooled to −30° C. 294 mg (12.3 mmol) 95% Sodium hydride were added, the mixture allowed to warm to r.t. and stirred for 12 h. 10 ml Water were added and the residue dissolved in dichloromethane. The organic phase was dried over Na$_2$SO$_4$, solvents removed and the remaining material purified by chromatography on silica gel (ethyl acetate/n-heptane 1:1) to yield 1.33 g (79%) yellow oil.

MS: M=298.0 (M+Na$^+$, APCI+).

$^1$H-NMR(400 MHz, D$_6$-DMSO): δ=2.86(t, 2H, CH$_2$—CH$_2$-triazole), 3.65(s, 2H, OCH$_2$PH), 4.55(m, 4H, OCH$_2$-vinyl, CH$_2$-triazole), 5.25(d, 1H,=CH$_2$), 5.38(d, 1H,=CH$_2$), 6.05(m, 1H, CH=CH$_2$), 6.90(d, 2H, 2'-/6'-H), 7.22(d, 2H, 3'-/5'-H), 7.73(s, 1H, triazole).

iv) 1-[2-(4-Allyloxy-phenylmethanesulfinyl)-ethyl]-1H-[1,2,3]triazole

A solution of 1.86 g (8.29 mmol) 77% 3-chloroperbenzoic acid in 40 ml ethyl acetate was added at -30° C. within 20 min. to a solution of 1.90 g (6.90 mmol) 1-[2-(4-allyloxy-benzylsulfanyl)-ethyl]-1H-[1,2,3]triazole in 160 ml dichloromethane and stirred for 1 h. The mixture was allowed to warm to r.t. washed with sat. NaHCO$_3$-solution, water and evaporated. The residue was purified by chromatography on silica gel (ethyl acetate/methanol 5:1) to give 1.25 g of the title compound as white powder.

MS: M=(ESI+)

$^1$H-NMR(400 MHz, D$_6$-DMSO): δ=3.11(dt, 1H, CH$_2$—CH$_2$-triazole), 3.32(dt, 1H, CH$_2$-CH$_2$triazole), 3.94.1 (d, 1H, SO$_2$CH$_2$Ph), 4.12(d, 1H, SO$_2$CH$_2$Ph), 4.56(d, 2H, OCH$_2$-vinyl), 4.78(m, 2H, CH$_2$-triazole), 5.26(d, 1H,=CH$_2$), 5.39(d, 1H,=CH$_2$), 6.02(m, 1H, CH=CH$_2$), 6.95(d, 2H, 2'-/6'-H), 7.22(d, 2H, 3'-/5'-H), 7.75(s, 1H, triazole), 8.16(s, 1H, triazole).

v) 4-(2-[1,2,3]Triazol-1-yl-ethanesulfinylmethyl)-phenol

A solution of 1.00 g (3.43 mmol) 1-[2-(4-allyloxy-phenylmethanesulfinyl)-ethyl]-1H-[1,2,3]triazole in 60 ml dichloromethane was added to a solution of 1.61 g (10.3 mmol) 1,3-dimethylbarbituric acid and 102 mg (0.09 mmol) Pd(PPh$_3$)$_4$ in 30 ml dichloromethane and stirred for 5 h at 50° C. The mixture was extracted with 3×50 ml sat. NaHCO$_3$-solution and 20 ml water. The organic phase was discarded and the aqueous phase acidified with 2M HCl to pH=4, concentrated to a volume of 50 ml and adjusted to pH=1. After five extractions with ethyl acetate, the organic extracts were combined and dried over MgSO$_4$. After evaporation the residue was purified by chromatography on silica gel (dichloromethane/methanol 100:2) to yield 0.84 g (97%) of the title compound.

$^1$H-NMR(400 MHz, D$_6$-DMSO): δ=3.11(dt, 1H, CH$_2$-CH$_2$-triazole), 3.29(dt, 1H, CH$_2$—CH$_2$-triazole), 3.90(d, 1H, SO$_2$CH$_2$Ph), 4.06(d, 1H, SO$_2$CH$_2$Ph), 4.77(m, 2H, CH$_2$-triazole), 6.74(d, 2H, 2'-/6'-H), 7.10(d, 2H, 3'-/5'-H), 7.74(s, 1H, triazole), 8.16(s, 1H, triazole), 9.49(s, 1H, OH).

vi) 1-[2-(4-{2-[(E)-2-(4-Trifluoromethanesulfinyl-phenyl)-vinyl]-oxazol-4-ylmethoxy}-phenylmethanesulfinyl)-ethyl]-1H-[1,2,3]triazole 14 mg (0.55 mmol) 95% sodium hydride were given to a solution of 126 mg (0.50 mmol) 4-(2-[1,2,3]triazol-1-yl-ethanesulfinylmethyl)-phenol in 4.0 ml DMF and stirred for 15 min. 168 mg (0.50 mmol) 4-Chloromethyl-2-[2-(4-trifluoromethanesulfinyl-phenyl)-vinyl]-oxazole were added and stirring continued at r.t. overnight. After addition of 6 ml water the resulting precipitate was collected and combined with additional material obtained by extraction of the aqueous phase at pH=3 with ethyl acetate, drying (sodium sulfate) and evaporation. Purification by chromatography on silica gel (eluent: ethyl acetate/methanol 9:1) gave 130 mg (77%) powder.

MS: M=551.0 (ESI+), 573.0(M+Na$^+$, ESI+).

$^1$H-NMR(400 MHz, D$_6$-DMSO): δ=3.12(dt, 1H, CH$_2$—CH$_2$-triazole), 3.36(dt, 1H, CH$_2$—CH$_2$-triazole), 3.96(d, 1H, SOCH$_2$Ph), 4.14(d, 1H, SOCH$_2$Ph), 5.04(s, 2H, OCH$_2$), 4.79 (m, 2H, CH$_2$-triazole), 7.05(d, 2H, 3'-/5'-H—Ar), 7.25(d, 2H; 2H, 2'-/6'-H—Ar), 7.39(d, 1H, vinyl-H), 7.64(d, 1H, vinyl-H), 7.75(s, 1H, triazole), 7.91(d, 2H, ArSOCF$_3$), 8.06(d, 2H, ArSOCF$_3$), 8.27(s, 1H, triazole), 8.31(s, 1H, oxazole).

EXAMPLE 10

1-[2-(4-{2-[(E)-2-(4-Trifluoromethanesulfinyl-phenyl)-vinyl]-oxazol-4-ylmethoxy}-phenylmethanesulfonyl)ethyl]-1H-[1,2,3]triazole i) 1-[2-(4-Allyloxy-phenylmethanesulfonyl)-ethyl]-1H-[1,2,3]triazole A solution of 13.3 g (21.6 mmol) oxone in 80 ml water was added within 20 min. to a solution of 2.00 g (7.20 mmol) 1-[2-(4-allyloxy-benzylsulfanyl)-ethyl]-1H-[1,2,3]triazole in 160 ml methanol and stirred for 24 h. The formed precipitate was dissolved in dichloromethane, washed with NaHCO$_3$-solution and dried over Na$_2$SO$_4$. Solvents were removed and the residue purified by chromatography on silica gel (ethyl acetate) to give the title compound as white powder (2.39 g, 90% purity, that were used for the next step without further purification). MS: M=308.3 (APCI+), 330.3 (M+Na$^+$, APCI+).

$^1$H-NMR(400 MHz, D$_6$-DMSO): δ=3.68(t, 2H, CH$_2$—CH$_2$-triazole), 4.41(s, 2H, SO$_2$CH$_2$PH), 4.57(d, 2H, OCH$_2$-vinyl), 4.80(t, 2H, CH$_2$-triazole), 5.26(d, 1H,=CH$_2$), 5.39(d, 1H, =CH$_2$), 6.04(m, 1H, CH=CH$_2$), 6.98(d, 2H, 2'-/6'-H), 7.29(d, 2H, 3'-/5'-H), 7.74(s, 1H, triazole), 8.18(s, 1H, triazole).

ii) 4-(2-[1,2,3] Triazol-1-yl-ethanesulfonylmethyl)-phenol

A solution of 2.39 g (7.78 mmol) 1-[2-(4-allyloxy-phenyl-methanesulfonyl)-ethyl]-1H-[1,2,3]triazole in 50 ml dichloromethane was added to a solution of 3.64 g (23.3 mmol) 1,3-dimethylbarbituric acid and 220 mg (0.19 mmol) Pd(PPh$_3$)$_4$ in 90 ml dichloromethane and stirred for 7 h at 40° C. The reaction mixture was washed with 3×80 ml sat. NaHCO$_3$-solution, 2×30 ml water and the water phase washed with 2×80 ml dichloromethane (discarded). The formed precipitate was collected, washed with water and ethyl acetate and dried to yield 0.86 g of product. The aqueous phase from above was acidified by acetic acid to pH=5 and extracted with ethyl acetate. After washing with water and drying over sodium sulphate the ethyl acetate extract was evaporated to give 1.45 g of an orange powder that was purified by chromatography on silica gel (eluent: ethyl acetate) to yield an additional amount of 0.47 g product. Combined yield: 1.33 g (58%).

MS: M=268.3 (ESI+), 290.3 (M+Na+, ESI+).

$^1$H-NMR(400 MHz, D$_6$-DMSO): δ=3.66(t, 2H, CH$_2$—CH$_2$-triazole), 4.34(s, 2H, SO$_2$CH$_2$PH), 4.79(t, 2H, CH$_2$-triazole), 6.77(d, 2H, 2'-/6'-H), 7.17(d, 2H, 3'-/5H), 7.74 (s, 1H, triazole), 8.18(s, 1H, triazole), 9.62(br, 1H, OH).

iii) 1-[2-(4-{2-[(E)-2-(-4-Trifluoromethanesulfinyl-phenyl)-vinyl]-oxazol-4-ylmethoxy}-phenyl-methanesulfonyl)-ethyl]-1H-[1,2,3]triazole 13.0 mg (0.50 mmol) 95% sodium hydride were given to a solution of 134 mg (0.50 mmol) 4-(2-[1,2,3]triazol-1-yl-ethanesulfonylmethyl)-phenol in 4.0 ml DMF and stirred for 15 min. 168 mg (0.50 mmol) 4-Chloromethyl-2-[2-(4-trifluoromethanesulfinyl-phenyl)-vinyl]-oxazole were added and stirring continued at r.t. overnight. After addition of 10 ml water the resulting precipitate was purified by chromatography on silica gel (eluent: dichloromethane/acetone 20:1) to give 11 mg product.

MS: M=567.0 (ESI+), 589.0 (M+Na+, ESI+).

$^1$H-NMR(400 MHz, D$_6$-DMSO): δ=3.70(t, 2H, CH$_2$—CH$_2$-triazole), 4.42(s, 2H, SO$_2$CH$_2$-Ph), 4.82(t, 2H, CH$_2$-triazole), 5.06(s, 2H, OCH$_2$-oxazole), 7.08(d, 2H, 3'-/5'-H—Ar), 7.31(d, 2H; 2H, 2'-/6'-H—Ar), 7.39(d, 1H, vinyl-H), 7.64(d, 1H, vinyl-H), 7.84(s, 1H, triazole), 7.91(d, 2H, ArSO$_2$), 8.06(m, 3H, ArSO$_2$,triazole), 8.28(s, 1H, oxazole).

EXAMPLE 11

1-[4-(4-{2-[2-(4-Trifluoromethanesulfinyl-phenyl)-vinyl]-oxazol-4-ylmethoxy}-phenyl)-but-3-enyl]-1H-[1,2,3]triazole i) 1-But-3-enyl-1H-[1,2,3]triazole 1H-[1,2,3]Triazole (10.36 g, 0.15 mol), sodium hydroxide (6 g, 0.15 mol) and potassium iodide (2.49 g, 0.015 mol) were dissolved in 2-methyl-2-butanol (50 ml) and heated to reflux for 1 h. At this temperature 4-bromo-but-1-ene (20.25 g, 0.15 mol) in 2-methyl-2-butanol (20 ml) were added dropwise and the resulting mixture was heated at reflux temperature for 4 h. After removal of the solvent the residue was taken up in ethyl acetate (100 ml), washed with water (3×50 ml), dried over sodium sulfate and concentrated. The crude product was purified by distillation yielding 0.65 g 2-but-3-enyl-2H-[1,2,3]triazole (b.p. 90-100° C. at 10 mbar), $^1$H-NMR (400 MHz, [D$_6$]-DMSO): δ=2.62(q, 2H, CH$_2$-CH=CH$_2$), 4.48(t, 2H, , CH$_2$-triazole), 4.97-5.06(m, 2H, CH$_2$—CH=CH$_2$), 5.75(m, CH$_2$-CH=CH$_2$), 7.75(s, 2H, triazole) and 6.36 g (34%) 1-but-3-enyl-1H-[1,2,3]triazole (b.p. 106-108° C. at 10 mbar) as a colorless liquid.

$^1$H-NMR (400 MHz, [D$_6$]-DMSO): δ=2.59(q, 2H, CH$_2$—CH=CH$_2$), 4.45(t, 2H, CH$_2$-triazole), 5.00-5.06(m, 2H, CH$_2$—CH=CH$_2$), 5.76(m, 1H, CH$_2$—CH=CH$_2$), 7.70(s, 1H, triazole), 8.10(s, 1H, triazole).

ii) 4-(4-[1,2,3]Triazol-1-yl-but-1-enyl)-phenol

A mixture of 3.00 g (24.4 mmol) 1-but-3-enyl-1H-[1,2,3] triazole, 6.79 g (20.3 mmol) tert-butyl-(4-iodo-phenoxy)-dimethyl-silane, 1.07 g (4.06 mmol) triphenylphosphine, 0.685 g (3.05 mmol) palladium(II)acetate and 56 ml triethylamine was heated to reflux for 24 h. The reaction mixture was cooled to r.t., evaporated, stirred with ice and adjusted to pH=1 by addition of conc. HCl. The organic material was collected with ethyl acetate/dichloromethane 1:2, the organic phase dried over sodium sulfate and evaporated. The residue was stirred with 20.3 ml 1M solution of tetrabutylammonium fluoride solution in THF at 28° C. for 3 h. After removal of THF, the residue was dissolved in dichloromethane, washed with water, evaporated and purified by chromatography on silica gel (ethyl acetate/n-heptane 5:1). The product containing fractions were collected, evaporated and stirred with little ethyl acetate/n-heptane 3:1 to yield 1.53 g (29%).

MS: M=216.3 (ESI+).

$^1$H-NMR(400 MHz, D$_6$-DMSO): δ=2.69(q, 2H, CH$_2$—CH=CH—Ar), 4.49(t, 2H, CH$_2$-triazole), 5.97(dt, 1H, CH=CH—Ar), 6.28(d, 1H, CH=CH—Ar), 6.68(d, 2H, 2'-/6'-H), 7.14(d, 2H, 3'-/5'-H), 7.69 (s, 1H, triazole), 8.12 (s, 1H, triazole), 9.42(s, 1H, OH).

iii) 1-[4-(4-{2-[2-(4-Trifluoromethanesulfinyl-phenyl)-vinyl]-oxazol-4-ylmethoxy}-phenyl)-but-3-enyl]-1H-[1,2,3] triazole 13 mg (0.50 mmol) 95% sodium hydride were given to a solution of 108 mg (0.50 mmol) 4-(4-[1,2,3]triazol-1-yl-but-1-enyl)-phenol in 4.0 ml DMF and stirred for 15 min. 168 mg (0.50 mmol) 4-chloromethyl-2-[2-(4-trifluoromethanesulfinyl-phenyl)-vinyl]-oxazole were added and stirring continued at r.t. overnight. After addition of 10 ml water the resulting precipitate was collected, washed with water (2×10 ml), methanol (2×10 ml), diethyl ether and dried in vacuum to yield 116 mg (45%) of product.

MS: M=515.1 (ESI+).

$^1$H-NMR(400 MHz, D$_6$-DMSO): δ=2.71(dt, 2H, CH$_2$—C=CH), 4.51(t, 2H, , CH$_2$(t, 2H, , CH$_2$-triazole), 5.02 (s, 2H, OCH$_2$-oxazole), 6.07(d, 1H, CH=CH—Ar), 6.34(dt, 1H, , CH=CH—Ar), 6.98(d, 2H, 3'-/5'-H—Ar), 7.29(d, 2H; 2H, 2'-/6'-H—Ar) 7.38(d, 1H, vinyl-H), 7.70(s, 1H, triazole), 7.91(d, 2H, ArSOCF$_3$), 8.06(d, 2H, ArSOCF$_3$), 8.13(s, 1H, triazole), 8.26(s, 1H, oxazole).

EXAMPLE 12

1-[4-(4-{2-[2-(4-Trifluoromethanesulfinyl-phenyl)-vinyl]-oxazol-4-ylmethoxy}-phenyl)-but-3-ynyl]-1H-[1,2,3]triazole i) 1-But-3-ynyl-1H-[1,2,3]triazole But-3-yn-1-ol (49.57 g, 707.2 mmol) and triethylamine (107.7 mL, 777 mmol, dried over KOH) were dissolved in dry dichloromethane (500 mL) under a nitrogen atmosphere and cooled to 0° C. Methanesulfonyl chloride (54.8 mL, 708 mmol), dissolved in 500 mL of dry dichloromethane was added within 90 minutes while keeping the temperature below 5° C. The mixture was stirred for 3.5 hours at room temperature, then poured onto 2.5 L of ice water. The organic phase was separated and washed with 2×500 mL of water and 1×250 mL of brine and dried over sodium sulfate. The volatiles were removed to yield 94.18 g of the methane sulfonate (631.2 mmol, 89.2%) as a yellow liquid.

A suspension of NaOH (37.86 g, 946.5 mmol), sodium iodide (94.65 g, 631.5 mmol) and 1H-[1,2,3]Triazole (61.03 g, 883.6 mmol) in 2-methyl-2-butanol (750 mL) was refluxed for 1 h under an inert atmosphere. After cooling to room temperature the methane sulfonate (94.18 g, 631.2 mmol) was added within 5 minutes. The resulting suspension was then heated to reflux for 3 hours, cooled to room temperature and concentrated on a rotary evaporator at 45° C.

Water (500 mL) and dichloromethane (1 L) were added and the organic phase was separated, dried over sodium sulfate and the volatiles removed at 30° C. The residue was distilled at 1.5 mbar. A forerun was collected at 20-70° C. The main fraction distilled at 123-129° C. as a colorless, turbid liquid.

After filtration over Celite (a pad of diatomite) 1-But-3-ynyl-1H-[1,2,3]triazole was obtained as a colorless liquid (29.8 g, 40%).

The content according to GC/FID was >98%.

$^1$H-NMR (CDCl$_3$) δ=2.05 (t, 1H, C≡CH), 2.75 (dt, 2H, CH$_2$—C≡CH), 4.5 (t, 2H, CH$_2$-triazole), 7.65 (s, 1H, triazole), 7.70 (s, 1H, triazole).

ii) 1-{4-[4-(tert-Butyl-dimethyl-silanyloxy)-phenyl]-but-3-ynyl}-1H-[1,2,3]triazole A solution of 1.94 g (16.1 mmol) 1-but-3-ynyl-1H-[1,2,3] triazole in 14 ml THF was added dropwise at 0° C. to a suspension of 3.35 g (10.0 mmol) tert-butyl-(4-iodo-phenoxy)-dimethyl-silane, 190 mg (1.00 mmol) Cu(I)I and 562 mg (0.80 mmol) Pd(PPh$_3$)$_4$ in 16 ml THF, followed by addition of 7.1 ml (50 mmol) diisopropylamine. The mixture was stirred at room temperature for 20 h, 30 ml water added, extracted twice with dichloromethane and the organic phase dried over sodium sulphate. After evaporation and purification by chromatography on silica gel (ethyl acetate/n-heptane 1:1) 2.80 g (85%) product were obtained.

MS: M=328.3 (APCI+).
$^1$H-NMR(400 MHz, D$_6$-DMSO): δ=0.18(s, 6H, SiCH$_3$), 0.94(s, 9H, C(CH$_3$)$_3$), 2.99(t, 2H, CH$_2$—C≡C), 4.59(t, 2H, CH$_2$-triazole), 6.81(d, 2H, 3'-/5'-H), 7.21(d, 2H, 2'-/5'-H), 7.74(s, 1H, triazole), 8.20 (s, 1H, triazole).

iii) 4-(4-[1,2,3]Triazol-1-yl-but-1-ynyl)-phenol

A mixture of 1.00 g (3.05 mmol) 1-{4-[4-(tert-butyl-dimethyl-silanyloxy)-phenyl]-but-3-ynyl}-1H-[1,2,3]triazole and 3.05 ml 1M tetrabutylammonium fluoride solution in THF was stirred for 3 h. After evaporation the residue was dissolved in dichloromethane and washed with water that was acidified by acetic acid. The organic phase was dried, evaporated and purified by chromatography on silica gel (ethyl acetate) to give 612 mg (94%) of the title compound.

MS: M=214.1 (ESI+), 212.0(ESI−).
$^1$H-NMR(400 MHz, D$_6$-DMSO): δ=2.97(t, 2H, CH$_2$—C≡C), 4.58(t, 2H, CH$_2$-triazole), 7(d, 2H, 2'-/6'-H), 7.13 (d, 2H, 3'-/5'-H), 7.74 (s, 1H, triazole), 8.19 (s, 1H, OH).

iv) 1-[4-(4-{2-[2-(4-Trifluoromethanesulfinyl-phenyl)-vinyl]-oxazol-4-ylmethoxy}-phenyl)-but-3-ynyl]-1H-[1,2,3]triazole 25 mg (1.00 mmol) 95% sodium hydride were given to a solution of 214 mg (1.00 mmol) 4-(4-[1,2,3]triazol-1-yl-but.1-ynyl)-phenol in 8.0 ml DMF and stirred for 15 min. 336 mg (1.00 mmol) 4-chloromethyl-2-[2-(4-trifluoromethanesulfinyl-phenyl)-vinyl]-oxazole were added and stirring continued at r.t. overnight. After addition of 10 ml water the resulting precipitate was collected, washed with water (2×10 ml), methanol (2×10 ml), diethyl ether and dried in vacuo to yield 246 mg (48%) of product.

MS: M=513.0 (ESI+).
$^1$H-NMR(400 MHz, D$_6$-DMSO): δ=3.00(t, 2H, CH$_2$—C≡C), 4.60(t, 2H, CH$_2$-triazole), 5.05(s, 2H, OCH$_2$-oxazole), 7.02(d, 2H, 3'-/5'-H—Ar), 7.27(d, 2H; 2'-/6'-H—Ar) 7.38(d, 1H, vinyl-H), 7.64(d, 1H, vinyl-H), 7.74(s, 1H, triazole), 7.92(d, 2H, ArSOCF$_3$), 8.05(d, 2H, ArSOCF$_3$), 8.21(s, 1H, triazole), 8.27(s, 1H, oxazole).

EXAMPLE 13

N-(2-[1,2,3] Triazol-1-yl-ethyl)-4-{2-[2-(4-trifluoromethanesulfinyl-phenyl)-vinyl]-oxazol-4-yl-methoxy}-benzenesulfonamide i) [1,2,3]Triazol-1-yl-acetonitrile A mixture of 40 g (0.58 mol) 1H-[1,2,3]triazole and 94.34 g (0.29 mol) cesium carbonate in 500 ml butanone was stirred at 60° C. for 30 min, then 69.5 g (0.58 mol) bromoacetonitrile were added and stirring at 60° C. continued for another 5 hours. The solvent was evaporated, the residue mixed with water, and extracted thrice with 150 ml ethyl acetate. The combined organic phases were dried, evaporated, and the residue distilled in vacuo. The fraction distilling at 108° C. (0.03 mbar) was collected to yield 28.15 g (45%) [1,2,3] triazol-1-yl-acetonitrile as red oil.

H-NMR(400 MHz, D$_6$-DMSO): δ=5.82(s, 2H, CH$_2$), 7.85 (s, 1H, triazole), 8.29 (s, 1H, triazole).

ii) 2-[1,2,3]Triazol-1-yl-ethylamine

A solution of 7.5 g (69 mmol) [1,2,3]triazol-1-yl-acetonitrile in liquid ammonia containing THF was hydrogenated over 5 g Raney nickel at 120 bar and 90° C. The catalyst was filtered off, the solvent concentrated and the residue distilled. The fraction distilling at 91° C. (0.03 mbar) was collected to yield 4.3 g (55%) 2-[1,2,3]triazol-1-yl-ethylamine as colorless oil.

$^1$H-NMR(400 MHz, D$_6$-DMSO): δ=2.96(t, 2H, CH$_2$), 3.07 (br, 2H, NH$_2$), 4.33(t, 2H, CH$_2$), 7.71(s, 1H, triazole), 8.10 (s, 1H, triazole).

iii) 4-Hydroxy-benzenesulfonylchloride 5 g (21.5 mmol) sodium 4-hydroxy-benzenesulfonate dihydrate were suspended in 50 ml toluene and refluxed for 2 hours using a Dean-Stark trap (a water separator used in chemical reactions). The solvent was evaporated, replaced by 12.8 g (108 mmol) thionyl chloride and 160 mg DMF and the mixture stirred for 4 hours at 60° C. and over night at room temperature. After evaporation, the residue was quenched with ice water, extracted thrice with dichloromethane and the extracts died and evaporated. Yield 4.78 g (quant.) raw product as white gum.

$^1$H-NMR(400 MHz, D$_6$-DMSO): δ=6.71(d, 2H, Ar—H), 7.43(d, 2H, Ar—H), 12.9(br, 1H, OH).

iv) 4-Hydroxy-N-(2-[1,2,3]triazol-1-yl-ethyl)-benzenesulfonamide

To a mixture of 9.31 g (83.1 mmol) 2-[1,2,3]triazol-1-yl-ethylamine and 13.96 g (166 mmol) sodium hydrogencarbonate in 320 ml THF was added dropwise a solution of 16.0 g (83.1 mmol) 4-hydroxy-benzenesulfonylchloride in 160 ml THF at room temperature. Stirring was continued at 80° C. for 4 hours, then the solvent was evaporated and the residue triturated with 100 ml water to leave 16.05 g (72%) title compound as white solid melting at 220-223° C. (dec).

MS: M=269.1(API+)
$^1$H-NMR(400 MHz, D$_6$-DMSO): δ=3.15(t, 2H, CH$_2$), 4.42 (t, 2H, CH$_2$), 6.90(d, 2H, Ar—H), 7.60(d, 2H, Ar—H), 7.64 (br, 1H, NH), 7.68(s, 1H, triazole), 8.06(s, 1H, triazole), 10.3(br, 1H, OH).

v) N-(2-[1,2,3] Triazol-1-yl-ethyl)-(4-{2-[(E)-2-(4-trifluoromethanesulfinyl-phenyl)-vinyl]-oxazol-4-ylmethoxy}-benzenesulfonamide A mixture of 145 mg (0.54 mmol) 4-hydroxy-N-(2-[1,2,3] triazol-1-yl-ethyl)-benzenesulfone-amide and 117 mg (0.36 mmol) cesium carbonate in 10 ml butanone was stirred at 60° C. for 30 min, then 201 mg (0.6 mmol) 4-chloromethyl-2-[2-(4-trifluoromethanesulfinyl-phenyl-vinyl]-oxazole and 100 mg (0.6 mmol) potassium iodide were added and stirring at 60° C. continued overnight. After evaporation, the residue was mixed with 15 ml water and extracted thrice with 15 ml ethyl acetate. The combined extracts were dried, evaporated and the product purified on silica. Elution with heptane/ethyl acetate 1:5 yielded 92 mg (27%) N-(2-[1,2,3]triazol-1-yl-ethyl)-(4-{2-[((E)-2-(4-trifluoromethanesulffinyl-phenyl)-vinyl]-oxazol-4-ylmethoxy}-benzene-sulfonamide as white solid melting at 172-174° C.

MS: M=568.0(ESI+)

¹H-NMR(400 MHz, D₆-DMSO): δ=3.19(t, 2H, CH₂), 4.43 (t, 2H, CH₂), 5.15(s, 2H, OCH₂), 7.23(d, 2H, Ar—H), 7.39(d, 1H, vinyl), 7.65(d, 1H, vinyl), 7.71(m, 3H, 2Ar—H +triazole), 7.77(t, 1H, NH), 7.91(d, 2H, Ar—H), 8.06(s, 3H, 2Ar—H +triazole), 8.31(s, 1H, oxazole).

EXAMPLE 14

1-[3-(4-{2-[2-(4-Trifluoromethanesulfinyl-phenyl)-vinyl]-oxazol-4-ylmethoxy}-phenoxy)-propyl]-1H-[1,2,3]triazole 14 mg (0.55 mmol) 95% sodium hydride were given to a solution of 110 mg (0.50 mmol) 4-(3-[1,2,3]triazol-1-yl-propoxy)-phenol in 4.0 ml DMF and stirred for 15 min. 168 mg (0.50 mmol) 4-chloromethyl-2-[2-(4-trifluoromethanesulfinyl-phenyl)-vinyl]-oxazole were added and stirring continued at r.t. overnight. After addition of 8 ml water the resulting precipitate was collected and purified by chromatography on silica gel (eluent: ethyl acetate/n-heptane 4:1) to yield 70 mg (27%) colorless powder.

MS: M=518.8 (ESI+)

¹H-NMR(400 MHz, D₆-DMSO): δ=2.26(quintet, 2H, CH₂—CH₂-triazole), 3.90(t, 2H, OCH₂CH₂—CH₂-triazole), 4.55(t, 2H, CH₂-triazole), 4.96(s, 2H, OCH₂-oxazole), 6.87 (d, 2H, Ar—H), 6.97(d, 2H, Ar—H) 7.38(d, 1H, vinyl-H), 7.63(d, 1H, vinyl-H), 7.73(s, 1H, triazole), 7.91(d, 2H, ArSOCF₃), 8.06(d, 2H, ArSOCF₃), 8.15(s, 1H, triazole), 8.23 (s, 1H, oxazole).

EXAMPLE 15

1-[4-(4-{2-[(E)-2-(4-Trifluoromethanesulfinyl-phenyl)-vinyl]-thiazol-4-ylmethoxy}-phenyl)-butyl]-1H-[1,2,3]triazole i) 3-(4-Trifluoromethylsulfanyl-phenyl)-acrylthioamide A mixture of 4.60 g (18.6 mmol) 3-(4-trifluoromethylsulfanyl-phenyl)-acrylamide and 0.92 g (4.1 mmol) phosphorous pentasulfide in 140 ml dioxane was stirred under reflux for 90 min. After evaporation, the residue was purified on silica. Elution with ethyl acetate/heptane 1:1 yielded 2.0 g (41%) 3-(4-trifluoromethylsulfanyl-phenyl)-acrylthioamide as yellow crystals melting at 143-144° C.

MS: M=262.0(ESI−)

¹H-NMR(400 MHz, D₆-DMSO): δ=7.09(d, 1H,=CH), 7.65(d, 1H,=CH), 7.74(m, 4H, Ar—H), 9.34(s, 1H, NH), 9.67(s, 1H, NH).

ii) 4-Chloromethyl-2-[2-(4-trifluoromethylsulfanyl-phenyl)-vinyl]-thiazole 2.00 g (7.6 mmol) 3-(4-trifluoromethylsulfanyl-phenyl)-acrylthioamide, 2.90 g (22.8 mmol) 1,3-dichloroacetone and 60 ml acetone were stirred at room temperature for 4 days, then refluxed for 4 h. The product was precipitated by addition of water, isolated and dried, and purified on silica. Elution with ethyl acetate/heptane 1:1 yielded 1.80 g (71%) 4-chloromethyl-2-[2-(4-trifluoromethylsulfanyl-phenyl)-vinyl]-thiazole as yellow solid, melting at 133-134° C.

MS: M=336.0(ESI+)

¹H-NMR(400 MHz, D₆-DMSO): δ=4.85(s, 2H, CH₂), 7.56(d, 1H,=CH), 7.65(d, 1H, =CH), 7.74(d, 2H, Ar—H), 7.78(s, 1H, thiazole), 7.87(d, 2H, Ar—H).

iii) 4-Chloromethyl-2-[2-(4-trifluoromethanesulfinyl-phenyl)-vinyl]-thiazole

A solution of 0.50 g (1.5 mmol) 4-chloromethyl-2-[2-(4-trifluoromethylsulfanyl-phenyl)-vinyl]-thiazole in 20 ml dichloromethane was stirred with 0.31 g (1.8 mmol) 3-chloro-benzenecarboperoxoic acid at room temperature for 2 days. The solution was washed with diluted sodium hydroxide, dried, evaporated and purified on silica. Elution with ethyl acetate/heptane 1:6 yielded 270 mg (52%) 4-chloromethyl-2-[2-(4-trifluoromethanesulfinyl-phenyl)-vinyl]-thiazole as off-white solid, melting at 98-99° C.

MS: M=351.9(ESI+)

¹H-NMR(400 MHz, D₆-DMSO): δ=4.86(s, 2H, CH₂), 7.62(d, 1H,=CH), 7.73(d, 1H, =CH), 7.75(s, 1H, thiazole), 7.91(d, 2H, Ar—H), 8.05(d, 2H, Ar—H).

iv) 1-[4-(4-{2-[(E)-2-(4-trifluoromethanesulfinyl-phenyl)-vinyl]-thiazol-4-ylmethoxy}-phenyl)-butyl]-1H-[1,2,3]triazole A mixture of 0.11 g (0.49 mmol) 4-(4-[1,2,3]triazol-1-yl-butyl)-phenol and 0.10 g (0.30 mmol) cesium carbonate in 10 ml butanone was stirred at 60° C. for 30 min, then 0.15 g (0.49 mmol) 4-chloromethyl-2-[2-(4-trifluoromethanesulfinyl-phenyl)-vinyl]-thiazole and 0.08 g (0.49 mmol) potassium iodide were added and stirring at 60° C. continued for 3 days. After evaporation, 15 ml water was added and the mixture extracted with two portions of 15 ml ethyl acetate. The combined organic layers were washed with 1N sodium hydroxide and water, dried over sodium sulfate and evaporated to give, after purification on silica (ethyl acetate/heptane 1:1, then ethyl acetate) 90 mg (34%) 1-[4-(4-{2-[(E)-2-(4-trifluoromethanesulfinyl-phenyl)-vinyl]-thiazol-4-ylmethoxy}-phenyl)-butyl]-1H-[1,2,3]triazole as white crystals melting at 118-119° C.

MS: M=532.9(ESI+)

¹H-NMR(400 MHz, D₆-DMSO): δ=1.49(quintet, 2H, CH₂), 1.81(quintet, 2H, CH₂), 2.51(t, 2H, CH₂), 4.39(t, 2H, CH₂-triazole), 5.16(s, 2H, CH₂O), 6.96(d, 2H, Ar—H), 7.10 (d, 2H, Ar—H), 7.62(d, 1H,=CH), 7.71(s, 1H, triazole), 7.73 (d, 1H,=CH), 7.75(s, 1H, thiazole), 7.91(d, 2H, Ar—H), 8.04 (d, 2H, Ar—H), 8.11(s, 1H, triazole).

EXAMPLE 16

1-[4-(4-{2-[2-(4-Trifluoromethanesulfinyl-phenyl)-vinyl]-oxazol-4-ylmethanesulfonyl}-phenyl)-butyl]-1H-[1,2,3]triazole i) 4-(4-Bromo-benzenesulfonylmethyl)-2-[2-(4-trifluoromethanesulfinyl-phenyl)-vinyl]-oxazole A solution of 4-chloromethyl-2-[2-(4-trifluoromethanesulfinyl-phenyl)-vinyl]-oxazole (0.5 g, 1.5 mmol) and sodium 4-bromobenzenesulfinate (0.72 g, 3 mmol) in N,N-dimethyl formamide (20 ml) was stirred for 3 h at 60° C. After cooling the mixture was poured onto water, extracted with ethyl acetate (3×50 ml), the combined organic layers were washed with water, dried over sodium sulfate, concentrated in vacuo and crystallized from ether yielding 4-(4-bromo-benzenesulfonylmethyl)-2-[2-(4-trifluoromethanesulfinyl-phenyl)-vinyl]-oxazole as white crystalline product. Yield 0.6 g (77%)

MS: M=521.8 (API+)

¹H-NMR(400 MHz, CDCl₃); δ=4.37 (s, 2H), 6.96 (d, 1H), 7.48 (d, 1H), 7.69-7.73 (m, 7H), 7.82 (d, 2H)

ii) 1-[4-(4-{2-[2-(4-Trifluoromethanesulfinyl-phenyl)-vinyl]-oxazol-4-ylmethanesulfonyl}-phenyl)-butyl]-1H-[1,2,3]triazole A solution of 1-but-3-enyl-1H-[1,2,3]triazole (0.14 g, 1.14 mmol) in anhydrous THF (10 ml) was treated with 9-BBN (0.5 M in THF, 5 ml, 2.5 mmol) at 0° C. and stirred for 2 h at room temperature. This mixture was added to a solution of 4-(4-bromo-benzenesulfonylmethyl)-2-[2-(4-trifluoromethanesulfinyl-phenyl)-vinyl]-oxazole (0.6 g, 1.15 mmol), [Pd(dppf)Cl$_2$] (98 mg, 0.12 mmol) and aqueous cesium carbonate (3M, 1.15 ml, 3.45 mmol) in N,N-dimethyl formamide (7 ml) and stirred for 3 h at 70° C. After cooling to room temperature ethyl acetate (100 ml) was added and the solution washed with water (2×50 ml). The organic layer was concentrated and the crude product purified by flash column chromatography (ethyl acetate) and crystallization from diethyl ether to yield 1-[4-(4-{2-[2-(4-trifluoromethanesulfinyl-phenyl)-vinyl]-oxazol-4-ylmethanesulfonyl}-phenyl)-butyl]-1H-[1,2,3]triazole as white solid (0.36 g, 55%).

MS: M=565.0 (API+).

$^1$H-NMR(400 MHz, CDCl$_3$); δ=1.67 (quintet, 2H), 1.95 (quintet, 2H), 2.73 (t, 2H), 4.36 (s, 2H), 4.40 (t, 2H), 6.98 (d, 1H), 7.31 (d, 2H), 7.50 (d, 1H), 7.50 (s, 1H), 7.71-7.76 (m, 6H), 7.82 (d, 2H).

EXAMPLE 17

1-[2-(4-{2-[(E)-2-(4-Trifluoromethanesulfonyl-phenyl)-vinyl]-oxazol-4-ylmethoxy}-phenylmethanesulfinyl)-ethyl]-1H-[1,2,3]triazole 14 mg (0.55 mmol) 95% sodium hydride were given to a solution of 126 mg (0.50 mmol) 4-(2-[1,2,3]triazol-1-yl-ethanesulfinylmethyl)-phenol in 3.0 ml DMF and stirred for 15 min. 168 mg (0.50 mmol) 4-Chloromethyl-2-[2-(4-trifluoromethanesulfonyl-phenyl)-vinyl]-oxazole were added and stirring continued at r.t. overnight. After addition of 6 ml water the resulting precipitate was purified by chromatography on silica gel (eluent: ethyl acetate/methanol 9:1).

MS: M=566.8 (ESI+), 588.8(M+Na$^+$, ESI+).

$^1$H-NMR(400 MHz, D$_6$-DMSO): δ=3.12(dt, 1H, CH$_2$—CH$_2$-triazole), 3.34(dt, 1H, CH$_2$—CH$_2$-triazole), 2H, OCH$_2$), 7.05(d, 2H, 3'-/5'-H—Ar), 7.25(d, 2H, 2'-/6'-H—Ar), 7.51(d, 1H, vinyl-H), 7.70(d, 1H, vinyl-H), 7.75(s, 1H, triazole), 8.13(s, 1H, triazole), 8.15(m, 4H, ArSO$_2$CF$_3$), 8.31(s, 1H, oxazole).

EXAMPLE 18

1-[4-(2-Methyl-4-{2-[(E)-2-(-4-trifluoromethanesulfinyl-phenyl)-vinyl]-oxazol-4-ylmethoxy}-phenyl-butyl]-1H-[1,2,3]triazole A mixture of 199 mg (0.86 mmol) 3-methyl-4-(4-[1,2,3]triazol-1-yl-butyl)-phenol and 169 mg (0.52 mmol) cesium carbonate in 10 ml butanone was stirred at 60° C. for 30 min, then 289 mg (0.86 mmol) 4-chloromethyl-2-[2-(4-trifluoromethanesulfinyl-phenyl)-vinyl]-oxazole and 143 mg (0.86 mmol) potassium iodide were added and stirring at 60° C. continued over night. After evaporation, 10 ml N,N-dimethylformamide and 20 ml water were added and the precipitate washed with water, methanol and ether. After chromatography on silica, eluent ethyl acetate, resulted 132 mg (29%) pure title compound as light yellow crystals melting at 113-114° C.

MS: M=531.1(ESI+)

$^1$H-NMR(400 MHz, D$_6$-DMSO): δ=1.43(quintet, 2H, CH$_2$), 1.86(quintet, 2H, CH$_2$), 2.21(s, 3H, CH$_3$), 2.51(t, 2H, CH$_2$), 4.41(t, 2H, CH$_2$), 4.97(s, 2H, OCH$_2$), 6.91(m, 2H, Ar—H), 7.01(d, 1H, Ar—H), 7.38(d, 1H, vinyl), 7.63(d, 1H, vinyl), 7.71(s, 1H, triazole), 7.91(d, 2H, Ar—H), 8.06(d, 2H, Ar—H), 8.12(s, 1H, triazole), 8.24(s, 1H, oxazole).

EXAMPLE 19

1-[4-(4-{2-[2-(4-Methanesulfinyl-phenyl)-vinyl]-oxazol-4-ylmethoxy}-phenyl)-butyl]-1H-1,2,3,]triazole i) 3-(4-Methylsulfanyl-phenyl)-acrylic acid A mixture of 50.70 g (0.33 mol) 4-methylsulfanyl-benzaldehyde, 39.65 g (0.38 mol) malonic acid 3.25 g (0.04 mmol) piperidine and 150 ml pyridine was kept at reflux temperature until carbon dioxide development ceased (5 h). The reaction mixture was poured into a solution of 750 ml ice water and 190 ml 6N HCl. The precipitate was isolated, washed with water, then with n-heptane and dried at 50° C. Yield: 60.0 g (93%) 3-(4-methylsulfanyl-phenyl)-acrylic acid as a light brown solid melting at 163-165° C.

$^1$H-NMR (400 MHz, D$_6$-DMSO): δ=2.51 (s, 3H), 6.48 (d, 16.2 Hz, 1H), 7.28 (d, 2H), 7.55 (d, 16.2Hz, 1H), 7.62 (d, 2H), 12.34 (broad, 1H)

ii) 3-(4-Methylsulfanyl-phenyl)-acrylamide

To a suspension of 5.00 g (25.7 mmol) 3-(4-methylsulfanyl-phenyl)-acrylic acid in 30.0 ml tetrahydrofuran and 0.3 ml N,N-dimethyl formamide a solution of 4.90 ml (38.6 mmol) oxalyl chloride in 5.0 ml tetrahydrofuran was added dropwise at 0° C. within 20 min. Stirring was continued at 0-5° C. for 30 min. and 3 h at room temperature thereafter. The resulting solution was cooled to 0-5° C. again and then added within 15 min. to 100 ml of a 25% aqueous ammonia solution. After evaporation of the organic solvent, 200 ml water were added and the solution cooled. The precipitated amide was collected, washed with water and n-heptane and dried at 40° C. in vacuo. Yield 4.46 g (90%) 3-(4-methylsulfanyl-phenyl)-acrylamide as an off-white solid melting at 193° C.

MS: M=194.2 (ES+)

$^1$H-NMR (400 MHz, D$_6$-DMSO): δ=2.50 (s, 3H), 6.57 (d, 16.2Hz, 1H), 7.07 (s, 2H), 7.28 (d, 2H), 7.38 (d, 16.2 Hz, 1H), 7.50 (d, 2H)

iii) 4-Chloromethyl-2-[2-(4-methylsulfanyl-phenyl)-vinyl]-oxazole 2.00 g (10.3 mmol) 3-(4-methylsulfanyl-phenyl)-acrylamide, 2.63 g (22.0 mmol) dichloro acetone and 60.0 ml xylene were kept at reflux temperature for 3 h with continuous removal of water by use of a Dean-Stark trap (a water separator used in chemical reactions). After removal of solvents in vacuo, the residue was partitioned between ethyl acetate and water. The organic extracts were dried and the solvent was distilled off. The remaining residue was purified by chromatography on silica gel (eluent: heptane/ethyl acetate 1:3). Yield: 1.50 g (55%) 4-Chloromethyl-2-[2-(4-methylsulfanyl-phenyl)-vinyl]-oxazole as a light yellow solid melting at 126-128° C.

MS: M=266.4 (ES+)

$^1$H-NMR (400 MHz, D$_6$-DMSO): δ=2.51 (s, 3H), 4.70 (s, 2H), 7.10 (d, 16.2Hz, 1H), 7.28 (d, 2H), 7.49 (d, 16.2Hz, 1H), 7.65 (d, 2H), 8.15 (s, 1H)

iv) 4-Chloromethyl-2-[2-(4-methanesulfinyl-phenyl)-vinyl]-oxazole

To a solution of 500 mg (1.9 mmol) 4-Chloromethyl-2-[2-(4-methylsulfanyl-phenyl)-vinyl]-oxazole in 20 ml dichloromethane 392 mg (2.3 mmol) 3-chloro-benzenecarboperoxoic acid were added and the mixture was stirred at r. t. overnight. After washing with aqueous NaOH (1N) three times the organic phase was dried and evaporated. The remaining residue was purified by chromatography on silica gel (eluent: ethyl acetate). Yield: 370 mg (70%) 4-Chloromethyl-2-[2-(4-methylsulfinyl-phenyl)-vinyl]-oxazole as a light yellow solid melting at 104-106° C.

MS: M=282.4 (ES+) $^1$H-NMR (400 MHz, D$_6$-DMSO): δ=2.77 (s, 3H), 4.71 (s, 2H), 7.29 (d, 16.2Hz, 1H), 7.60 (d, 16.2Hz, 1H), 7.72 (d, 2H), 7.93 (d, 2H), 8.20 (s, 1H)

v) 1-[4-(4-{2-[2-(4-Methanesulfinyl-phenyl)-vinyl]-oxazol-4-ylmethoxy}-phenyl)-butyl]-1H-1,2,3]triazole A mixture of 154 mg (0.71 mmol) 4-(4-[1,2,3]triazol-1-yl-butyl)-phenol and 140 mg (0.43 mmol) cesium carbonate in 10 ml butanone was stirred at 60° C. for 30 min, then 200 mg (0.71 mmol) 4-chloromethyl-2-[2-(4-methanesulfinyl-phenyl)-vinyl]-oxazole and 118 g (0.71 mmol) potassium iodide were added and stirring at 60° C. continued overnight. After evaporation, 50 ml water was added and the mixture extracted with two portions of 50 ml ethyl acetate. The combined organic layers were washed with 1N sodium hydroxide and water, dried over sodium sulfate and evaporated. Chromatography on silica, eluent ethyl acetate/methanol 1:0 to 9:1, returned 160 mg (49%) pure title compound as light yellow crystals melting at 149-150° C.

MS: M=463.3 (ES+)
$^1$H-NMR (400 MHz, D$_6$-DMSO): δ=1.49 (quintet, 2H), 1.81 (quintet, 2H), 2.54 (t, 2H), 2.77 (s, 3H), 4.40 (t, 2H), 4.99 (s, 2H), 6.95 (d, 2H), 7.10 (d, 2H), 7.30 (d, 16.2 Hz, 1H), 7.60 (d, 16.2Hz, 1H), 7.66-7.79 (m, 3H), 7.93 (d, 2H), 8.11 (s, 1H) 8.22 (s, 1H)

EXAMPLE 20

1-[4-(2-Methyl-4-{2-[2-(4-trifluoromethanesulfonyl-phenyl)-vinyl]-oxazol-4-ylmethoxy}-phenyl)-butyl]-1H-[1,2,3]triazole A mixture of 132 mg (0.57 mmol) 3-methyl-4-(4-[1,2,3]triazol-1-yl-butyl)-phenol and 186 mg (0.57 mmol) cesium carbonate in 10 ml butanone was stirred at 60° C. for 30 min, then 200 mg (0.57 mmol) 4-chloromethyl-2-[2-(4-trifluoromethanesulfonyl-phenyl)-vinyl]-oxazole and 95 mg (0.57 mmol) potassium iodide were added and stirring at 60° C. continued over night. After evaporation, 50 ml water was added and the mixture extracted with two portions of 50 ml ethyl acetate. The combined organic layers were washed with 1N sodium hydroxide and water, dried over sodium sulfate and evaporated. Chromatography on silica, eluent ethyl acetate, returned 150 mg (49%) pure title compound as light yellow crystals melting at 140-142° C.

MS: M=547.6 (ESI+)
$^1$H-NMR(400 MHz, D$_6$-DMSO): δ=1.43 (quintet, 2H, CH$_2$), 1.87 (quintet, 2H, CH$_2$), 2.21 (s, 3H, CH$_3$), 2.51 (t, 2H, CH$_2$), 4.42 (t, 2H, CH$_2$), 4.99 (s, 2H, OCH$_2$), 6.79 (d, 1H, Ar—H), 6.82 (s, 1H, Ar—H), 7.01 (d, 1H, Ar—H), 7.51 (d, 1H, vinyl), 7.69 (d, 1H, vinyl), 7.72 (s, 1H, triazole), 8.05-8.24 (m, 5H, Ar—H, triazole), 8.28 (s, 1H, oxazole).

Unless stated to the contrary, all compounds in the examples were prepared and characterized as described. All ranges recited herein encompass all combinations and sub- combinations included within that range limit. All patents and publications cited herein are hereby incorporated by reference in their entirety.

The invention claimed is:
1. A compound of formula I

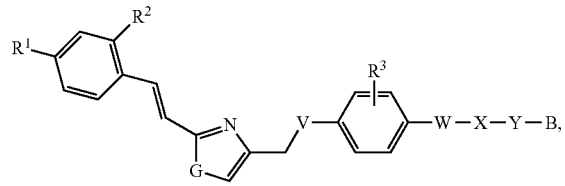

formula I wherein:
R$^1$ is selected from the group consisting of:
(a) —S(O)CH$_3$,
(b) —S(O)CF$_3$,
(c) S(O)$_2$CH$_3$, and
(d) S(O)$_2$CF$_3$;
R$^2$ is selected from the group consisting of:
(a) hydrogen,
(b) fluorine, and
(c) chlorine;
R$^3$ is selected from the group consisting of:
(a) hydrogen,
(b) (C$_1$-C$_3$)alkyl,
(c) (C$_1$-C$_3$)alkoxy, and
(d) halogen;
G is selected from the group consisting of:
(a) —NH—,
(b) —S—, and
(c) —O—;
V is selected from the group consisting of:
(a) —O—, and
(b) —S(O)$_x$—;
W is selected from the group consisting of:
(a) —CH$_2$—; and
(b) a direct bond;
X is selected from the group consisting of:
(a) —NH—,
(b) —O—,
(c) —S(O)$_x$—,
(d) —C(O)—,
(e) —C(O)NH—,
(f) —NHC(O)—,
(g) —S(O)$_2$NH—,
(h) —NHS(O)$_2$—,
(i) —CH═CH—,
(j) —C≡C—, and
(k) —CH$_2$—;
Y is —(CH$_2$)$_n$-;
B is selected from the group consisting of:
(a) imidazolyl, which is:
(1) unsubstituted; or
(2) once substituted with —C(O)OH; or
(3) one, two or three times substituted with alkyl, which alkyl is:
(A) optionally interrupted one, two, or three times by —O—, —S(O)$_x$—, —S(O)$_2$NH—, —NHS(O)$_2$—, —C(O)—NH—, —NH—C(O)—, or —P(O)(CH$_3$)—; and (B) unsubstituted or one, two or three times substituted with —OH, —NH$_2$, —C(O)OH, or —P(O)(CH$_3$)$_2$; or
(4) once substituted with —C(O)OH and one, two or three times substituted with alkyl, which alkyl is:
(A) optionally interrupted one, two, or three times by —O—, —S(O)$_x$—, —S(O)$_2$NH—, —NHS(O)$_2$—, —C(O)—NH—, —NH—C(O)—, or —P(O)(CH$_3$)—; and
(B) unsubstituted or one, two or three times substituted with —OH, —NH$_2$, —C(O)OH, or —P(O)(CH$_3$)$_2$;

(b) pyrazolyl, which is:
(1) unsubstituted; or
(2) once substituted with —C(O)OH; or
(3) one, two or three times substituted with alkyl, which alkyl is:
(A) optionally interrupted one, two, or three times by —O—, —S(O)$_x$—, —S(O)$_2$NH—, —NHS(O)$_2$—, —C(O)—NH—, —NH—C(O)—, or —P(O)(CH$_3$)—; and
(B) unsubstituted or one, two or three times substituted with —OH, —NH$_2$, —C(O)OH, or —P(O)(CH$_3$)$_2$; or
(4) once substituted with —C(O)OH and one, two or three times substituted with alkyl, which alkyl is:
(A) optionally interrupted one, two, or three times by —O—, —S(O)$_x$—, —S(O)$_2$NH—, —NHS(O)$_2$—, —C(O)—NH—, —NH—C(O)—, or —P(O)(CH$_3$)—; and
(B) unsubstituted or one, two or three times substituted with —OH, —NH$_2$, —C(O)OH, or —P(O)(CH$_3$)$_2$;

(c) triazolyl, which is:
(1) unsubstituted; or
(2) once substituted with —C(O)OH; or
(3) one, two or three times substituted with alkyl, which alkyl is:
(A) optionally interrupted one, two, or three times by —O—, —S(O)$_x$—, —S(O)$_2$NH—, —NHS(O)$_2$—, —C(O)—NH—, —NH—C(O)—, or —P(O)(CH$_3$)—; and
(B) unsubstituted or one, two or three times substituted with —OH, —NH$_2$, —C(O)OH, or —P(O)(CH$_3$)$_2$; or
(4) once substituted with —C(O)OH and one, two or three times substituted with alkyl, which alkyl is:
(A) optionally interrupted one, two, or three times by —O—, —S(O)$_x$—, —S(O)$_2$NH—, —NHS(O)$_2$—, —C(O)—NH—, —NH—C(O)—, or —P(O)(CH$_3$)—; and
(B) unsubstituted or one, two or three times substituted with —OH, —NH$_2$, —C(O)OH, or —P(O)(CH$_3$)$_2$; and (d) tetrazolyl, which is:
(1) unsubstituted; or
(2) once substituted with —C(O)OH; or
(3) one, two or three times substituted with alkyl, which alkyl is:
(A) optionally interrupted one, two, or three times by —O—, —S(O)$_x$—, —S(O)$_2$NH—, —NHS(O)$_2$—, —C(O)—NH—, —NH—C(O)—, or —P(O)(CH$_3$)—; and
(B) unsubstituted or one, two or three times substituted with —OH, —NH$_2$, —C(O)OH, or —P(O)(CH$_3$)$_2$; or
(4) once substituted with —C(O)OH and one, two or three times substituted with alkyl, which alkyl is:
(A) optionally interrupted one, two, or three times by —O—, —S(O)$_x$—, —S(O)$_2$NH—, —NHS(O)$_2$—, —C(O)—NH—, —NH—C(O)—, or —P(O)(CH$_3$)—; and
(B) unsubstituted or one, two or three times substituted with —OH, —NH$_2$, —C(O)OH, or —P(O)(CH$_3$)$_2$;

n is 1, 2 or 3; and
x is 0, 1 or 2;
or a pharmaceutically acceptable salt or ester thereof.

2. A compound according to claim 1, wherein:
$R^1$ is selected from the group consisting of:
(a) —S(O)CH$_3$,
(b) —S(O)CF$_3$,
(c) —S(O)$_2$CH$_3$, and
(d) —S(O)$_2$CF$_3$; and
G is —S— or —O—.

3. A compound according to claim 1, wherein:
$R^1$ is selected from the group consisting of:
(a) —S(O)CH$_3$,
(b) —S(O)CF$_3$,
(c) S(O)$_2$CH$_3$, and
(d) S(O)$_2$CF$_3$;
$R^2$ is hydrogen;
$R^3$ is hydrogen; and
G is —S— or —O—.

4. A compound according to claim 1, wherein:
$R^1$ is selected from the group consisting of:
(a) —S(O)CH$_3$,
(b) —S(O)CF$_3$,
(c) —S(O)$_2$CH$_3$, and
(d) —S(O)$_2$CF$_3$;
$R^2$ is hydrogen;
$R^3$ is hydrogen or methyl;
G is —O—; and
V is —O—.

5. A compound according to claim 1, wherein:
$R^1$ is —S(O)-CF$_3$ or —S(O)$_2$CF$_3$;
$R^2$ is hydrogen;
$R^3$ is hydrogen;
G is —O— or —S—;
V is —O— or —S(O)$_x$—;
—W—X—Y— is selected from the group consisting of:
(a) —(CH$_2$)$_4$—,
(b) —O—(CH$_2$)$_3$—,
(c) —C(O)—(CH$_2$)$_3$—,
(d) —S—(CH$_2$)$_3$—,
(e) —S(O)$_2$—(CH$_2$)$_3$—,
(f) —S(O)—(CH$_2$)$_3$—,
(g) —S(O)$_2$—NH—(CH$_2$)$_2$—,
(h) —NH—C(O)—(CH$_2$)$_2$—,
(i) —C(O)—NH—(CH$_2$)$_2$—,
(j) —CH$_2$—NH—(CH$_2$)$_2$—,
(k) —CH$_2$—O—(CH$_2$)$_2$—,
(l) —CH$_2$—S(O)—(CH$_2$)$_2$—,
(m) —CH$_2$—S(O)$_2$—(CH$_2$)$_2$—,
(n) —CH=CH—CH$_2$—,
(o) —CH=CH—(CH$_2$)$_2$—,
(p) —CH$_2$—CH=CH—CH$_2$—, and
(q) —C≡C—(CH$_2$)$_2$—;

B is selected from the group consisting of:
(a) imidazolyl, which is:
(1) unsubstituted; or
(2) one, two or three times substituted with alkyl, which alkyl is:

(A) optionally interrupted one, two, or three times by —O—, —S(O)$_x$—, —S(O)$_2$NH—, —NHS(O)$_2$—, —C(O)—NH—, —NH—C(O)—, or —P(O)(CH$_3$)—; and
(B) unsubstituted or one, two or three times substituted with —OH, —NH$_2$, —C(O)OH, or —P(O)(CH$_3$)$_2$;
(b) triazolyl, which is:
(1) unsubstituted; or
(2) one, two or three times substituted with alkyl, which alkyl is:
(A) optionally interrupted one, two, or three times by —O—, —S(O)$_x$—, —S(O)$_2$NH—, —NHS(O)$_2$—, —C(O)—NH—, —NH—C(O)—, or —P(O)(CH$_3$)—; and
(B) unsubstituted or one, two or three times substituted with —OH, —NH$_2$, —C(O)OH, or —P(O)(CH$_3$)$_2$; and
(c) tetrazolyl, which is:
(1) unsubstituted; or
(2) one, two or three times substituted with alkyl, which alkyl is:
(A) optionally interrupted one, two, or three times by —O—, —S(O)$_x$—, —S(O)$_2$NH—, —NHS(O)$_2$—, —C(O)—NH—, —NH—C(O)—, or —P(O)(CH$_3$)—; and
(B) unsubstituted or one, two or three times substituted with —OH, —NH$_2$, —C(O)OH, or —P(O)(CH$_3$)$_2$.

6. A compound according to claim 5 selected from the group consisting of:
1-[4-(4-{2-[(E)-2-(4-trifluoromethanesulfinyl-phenyl)-vinyl]-thiazol-4-ylmethoxy}-phenyl)-butyl]-1H-[1,2,3]triazole; and
1-[4-(4-{2-[2-(4-trifluoromethanesulfinyl-phenyl)-vinyl]-oxazol-4-ylmethanesulfonyl}-phenyl)-butyl]-1H-[1,2,3]triazole.

7. A compound according to claim 1, wherein:
$R^1$ is S(O)-CH$_3$ or —S(O)$_2$CH$_3$;
$R^2$ is hydrogen;
$R^3$ is hydrogen;
G is —O— or —S—;
V is —O—, or —S(O)$_x$—;
—W—X—Y— is selected from the group consisting of:
(a) —(CH$_2$)$_4$—,
(b) —O—(CH$_2$)$_3$—,
(c) —C(O)—(CH$_2$)$_3$—,
(d) —S—(CH$_2$)$_3$—,
(e) —S(O)$_2$—(CH$_2$)$_3$—,
(f) —S(O)—(CH$_2$)$_3$—,
(g) —S(O)$_2$—NH—(CH$_2$)$_2$—,
(h) —NH—C(O)—(CH$_2$)$_2$—,
(i) —C(O)—NH—(CH$_2$)$_2$—,
(j) —CH$_2$—NH—(CH$_2$)$_2$—,
(k) —CH$_2$—O—(CH$_2$)$_2$—,
(l) —CH$_2$—S(O)—(CH$_2$)$_2$—,
(m) —CH$_2$—S(O)$_2$—(CH$_2$)$_2$—,
(n) —CH=CH—CH$_2$—,
(o) —CH=CH—(CH$_2$)$_2$—,
(p) —CH$_2$—CH=CH—CH$_2$—, and
(q) —C≡C—(CH$_2$)$_2$—; and
B is selected from the group consisting of:
(a) imidazolyl, which is:
(1) unsubstituted; or
(2) one, two or three times substituted with alkyl, which alkyl is:
(A) optionally interrupted one, two, or three times by —O—, —S(O)$_x$—, —S(O)$_2$NH—, —NHS(O)$_2$—, —C(O)—NH—, —NH—C(O)—, or —P(O)(CH$_3$)—; and
(B) unsubstituted or one, two or three times substituted with —OH, —NH$_2$, —C(O)OH, or —P(O)(CH$_3$)$_2$;
(b) triazolyl, which is:
(1) unsubstituted; or
(2) one, two or three times substituted with alkyl, which alkyl is:
(A) optionally interrupted one, two, or three times by —O—, —S(O)$_x$—, —S(O)$_2$NH—, —NHS(O)$_2$—, —C(O)—NH—, —NH—C(O)—, or —P(O)(CH$_3$)—; and
(B) unsubstituted or one, two or three times substituted with —OH, —NH$_2$, —C(O)OH, or —P(O)(CH$_3$)$_2$; and
(c) tetrazolyl, which is:
(1) unsubstituted; or
(2) one, two or three times substituted with alkyl, which alkyl is:
(A) optionally interrupted one, two, or three times by —O—, —S(O)$_x$—, —S(O)$_2$NH—, —NHS(O)$_2$—, —C(O)—NH—, —NH—C(O)—, or —P(O)(CH$_3$)—; and
(B) unsubstituted or one, two or three times substituted with —OH, —NH$_2$, —C(O)OH, or —P(O)(CH$_3$)$_2$.

8. A compound according to claim 7 wherein the compound is:
1-[4-(4-{2-[(E)-2-(4-Methanesulfinyl-phenyl)-vinyl]-oxazol-4-ylmethoxy}-phenyl)-butyl]-1H-[1,2,3]triazole.

9. A compound according to claim 1, wherein:
$R^1$ is —S(O)—CF$_3$;
$R^2$ and $R^3$ are both hydrogen;
G and V are both —O—;
—W—X—Y— is selected from the group consisting of:
(a) —(CH$_2$)$_4$—,
(b) —O—(CH$_2$)$_3$—,
(c) —S(O)$_2$—NH—(CH$_2$)$_2$—,
(d) —CH$_2$—NH—(CH$_2$)$_2$—,
(e) —CH$_2$—O—(CH$_2$)$_2$—,
(f) —CH$_2$—S(O)—(CH$_2$)$_2$—,
(g) —CH$_2$—S(O)$_2$—(CH$_2$)$_2$—,
(h) —CH=CH—(CH$_2$)$_2$—, and
(i) —C≡C—(CH$_2$)$_2$—; and
B is selected from the group consisting of:
(a) unsubstituted triazolyl;
(b) unsubstituted tetrazolyl; and
(c) imidazolyl, which is (1) unsubstituted or (2) once substituted with 2-(2-hydroxyethoxy)ethyl, 1-hydroxyethyl, 2-hydroxyethyl, 2-(2-methoxy-ethoxy)-ethyl, hydroxymethyl, 2-methanesulfinyl-ethyl, 2-methanesulfonyl-ethyl, dimethyl-phosphinoylmethyl, methoxymethyl, carboxymethyl, 2-carboxyethyl, aminomethyl, 1-aminoethyl, or 2-aminoethyl.

10. A compound according to claim 9 selected from the group consisting of:
4-[4-(4-imidazol-1-yl-butyl)-phenoxymethyl]-2-[2-(4-trifluoromethanesulfinyl-phenyl)-vinyl]-oxazole;
2-{1-[4-(4-{2-[(E)-2-(4-trifluoromethanesulfinyl-phenyl)-vinyl]-oxazol-4-ylmethoxy}-phenyl)-butyl]-1H-imidazol-2-yl}-ethanol;
(2-[1,2,3]triazol-1-yl-ethyl)-(4-{2-[(E)-2-(4-trifluoromethanesulfinyl-phenyl)-vinyl]-oxazol-4-ylmethoxy}-benzyl)-amine;

1-[4-(4-{2-[2-(4-trifluoromethanesulfinyl-phenyl)-vinyl]-oxazol-4-ylmethoxy}-phenyl)-butyl]-1H-[1,2,3]triazole;

4-[4-(4-{2-[(E)-2-(4-trifluoromethanesulfinyl-phenyl)-vinyl]-oxazol-4-ylmethoxy}-phenyl)-butyl]-1H-[1,2,3] triazole;

5-[4-(4-{2-[(E)-2-(4-trifluoromethanesulfinyl-phenyl)-vinyl]-oxazol-4-ylmethoxy}-phenyl)-butyl]-2H-tetrazole;

1-[2-(4-{2-[-4-(trifluoromethanesulfinyl-phenyl)-vinyl]-oxazol-4-ylmethoxy}-benzyloxy)-ethyl]-1H-[1,2,3]-triazole;

1-[2-(4-{2-[(E)-2-(4-trifluoromethanesulfinyl-phenyl)-vinyl]-oxazol-4-ylmethoxy}-phenylmethanesulfinyl)-ethyl]-1H-[1,2,3]triazole;

1-[2-(4-{2-[(E)-2-(4-trifluoromethanesulfinyl-phenyl)-vinyl]-oxazol-4-ylmethoxy}-phenylmethanesulfonyl)-ethyl]-1H-[1,2,3]triazole;

1-[4-(4-{2-[2-(4-trifluoromethanesulfinyl-phenyl)-vinyl]-oxazol-4-ylmethoxy}-phenyl)-but-3enyl]-1H-[1,2,3] triazole;

1-[4-(4-{2-[2-(4-trifluoromethanesulfinyl-phenyl)-vinyl]-oxazol-4-ylmethoxy}-phenyl)-but-3ynyl]-1H-[1,2,3] triazole;

N-(2-[1,2,3]triazol-1-yl-ethyl)-4-{2-[(E)-2-(4-trifluoromethanesulfinyl-phenyl)-vinyl]-oxazol-4-yl-methoxy}-benzenesulfonamide; and 1-[3-(4-{2-[2-(4-trifluoromethanesulfinyl-phenyl)-vinyl]-oxazol-4-ylmethoxy}-phenoxy)-propyl]-1H-[1,2,3] triazole.

11. A compound according to claim 1, wherein:
$R^1$ is $-S(O)_2-CF_3$;
$R^2$ and $R^3$ are both hydrogen;
G and V are both —O—;
—W—X—Y— is selected from the group consisting of:
(a) —$(CH_2)_4$—,
(b) —O—$(CH_2)_3$—,
(c) —$S(O)_2$—NH—$(CH_2)_2$—,
(d) —$CH_2$—NH—$(CH_2)_2$—,
(e) —$CH_2$—O—$(CH_2)_2$—,
(f) —$CH_2$—$S(O)$—$(CH_2)_2$—,
(g) —$CH_2$—$S(O)_2$—$(CH_2)_2$—,
(h) —CH=CH—$(CH_2)_2$—, and
(i) —C≡C—$(CH_2)_2$—; and
B is triazolyl.

12. The compounds according to claim 11 selected from the group consisting of:
1-[4-(4-{2-[(E)-2-(4-trifluoromethanesulfonyl-phenyl)-vinyl]-oxazol-4-ylmethoxy}-phenyl)-butyl]-1H-[1,2,3] triazole; and
1-[2-(4-{2-[(E)-2-(4-trifluoromethanesulfinyl-phenyl)-vinyl]-oxazol-4-ylmethoxy}-phenylmethanesulfinyl)-ethyl]-1H-[1,2,3]triazole.

13. A compound according to claim 1, wherein:
$R^1$ is $-S(O)-CF_3$;
$R^2$ is hydrogen;
$R^3$ is methyl;
G and V are both —O—;
—W—X—Y— is selected from the group consisting of:
(a) —$(CH_2)_4$—,
(b) —O—$(CH_2)_3$—,
(c) —$S(O)_2$—NH—$(CH_2)_2$—,
(d) —$CH_2$—NH—$(CH_2)_2$—,
(e) —$CH_2$—O—$(CH_2)_2$—,
(f) —$CH_2$—$S(O)$—$(CH_2)_2$—,
(g) —$CH_2$—$S(O)_2$—$(CH_2)_2$—,
(h) —CH=CH—$(CH_2)_2$—, and
(i) —C≡C—$(CH_2)_2$—; and
B is selected from the group consisting of:
(a) unsubstituted triazolyl;
(b) unsubstituted tetrazolyl; and
(c) imidazolyl which is (1) unsubstituted or (2) once substituted with
2-(2-hydroxyethoxy)ethyl,
1-hydroxyethyl,
2-hydroxyethyl,
2-(2-methoxy-ethoxy)-ethyl,
hydroxymethyl,
2-methanesulfinyl-ethyl,
2-methanesulfonyl-ethyl,
dimethyl-phosphinoylmethyl,
methoxymethyl,
carboxymethyl,
2-carboxyethyl,
aminomethyl,
1-aminoethyl, or
2-aminoethyl.

14. A compound according to claim 13 wherein the compound is: 1-[4-(2-Methyl-4-{2-[(E)-2-(-4-trifluoromethanesulfinyl-phenyl)-vinyl]-oxazol-4-ylmethoxy}-phenyl)-butyl]-1H-[1,2,3]triazole.

15. A compound according to claim 1, wherein:
$R^1$ is $-S(O)_2-CF_3$;
$R^2$ is hydrogen;
$R^3$ is methyl;
G and V are both —O—;
—W—X—Y— is selected from the group consisting of:
(a) —$(CH_2)_4$—,
(b) —O—$(CH_2)_3$—,
(c) —$S(O)_2$—NH—$(CH_2)_2$—,
(d) —$CH_2$—NH—$(CH_2)_2$—,
(e) —$CH_2$—O—$(CH_2)_2$—,
(f) —$CH_2$—$S(O)$—$(CH_2)_2$—,
(g) —$CH_2$—$S(O)_2$—$(CH_2)_2$—,
(h) —CH=CH—$(CH_2)_2$—, and
(i) —C≡C—$(CH_2)_2$—; and
B is triazolyl.

16. A compound according to claim 15 wherein the compound is: 1-[4-(2-Methyl-4-{2-[(E)-2-(4-trifluoromethanesulfonyl-phenyl)-vinyl]-oxazol-4-ylmethoxy}-phenyl)-butyl]-1H-[1,2,3]triazole.

17. The process for the manufacture of a compound according to claim 1, wherein
a compound of formula III

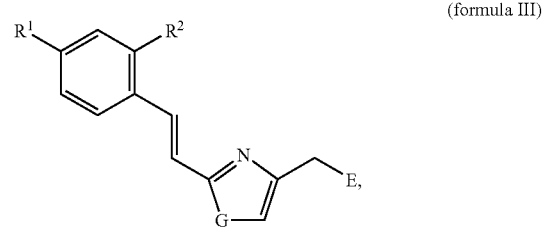

(formula III)

wherein $R^1$, $R^2$ and G have the meaning given in claim 1 and E denotes a suitable leaving group, is reacted with a compound of formula IV

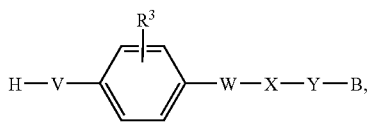
(formula IV)

wherein $R^3$, V, W, X, Y and B have the meaning given in claim 1; and wherein a protecting group, if present to protect the heteroatoms in the imidazole-, pyrazole-, triazole- or tetrazole ring of "B" from undesired side reactions, is cleaved.

18. A pharmaceutical composition comprising, (i) a therapeutically effective amount of a compound of formula I or a pharmaceutically acceptable salt or ester thereof, and (ii) a pharmaceutically acceptable carrier; wherein formula I is:

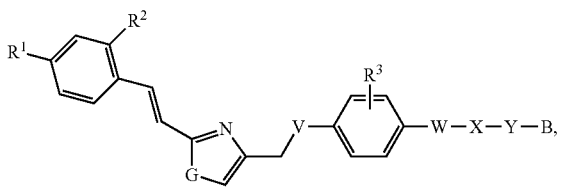
formula I wherein:
$R^1$ is selected from the group consisting of:
- (a) —S(O)CH$_3$,
- (b) —S(O)CF$_3$,
- (c) S(O)$_2$CH$_3$, and
- (d) S(O)$_2$CF$_3$;

$R^2$ is selected from the group consisting of:
- (a) hydrogen,
- (b) fluorine, and
- (c) chlorine;

$R^3$ is selected from the group consisting of:
- (a) hydrogen,
- (b) (C$_1$-C$_3$)alkyl,
- (c) (C$_1$-C$_3$)alkoxy, and
- (d) halogen;

G is selected from the group consisting of:
- (a) —NH—,
- (b) —S—, and
- (c) —O—;

V is selected from the group consisting of:
- (a) —O—, and
- (b) —S(O)$_x$—;

W is selected from the group consisting of:
- (a) —CH$_2$—; and
- (b) a direct bond;

X is selected from the group consisting of:
- (a) —NH—,
- (b) —O—,
- (c) —S(O)$_x$—,
- (d) —C(O)—,
- (e) —C(O)NH—,
- (f) —NHC(O)—,
- (g) —S(O)$_2$NH—,
- (h) —NHS(O)$_2$—,
- (i) —CH=CH—,
- (j) —C≡C—, and
- (k) —CH$_2$—;

Y is —(CH$_2$)$_n$-;

B is selected from the group consisting of:
(a) imidazolyl, which is:
  (1) unsubstituted; or
  (2) once substituted with —C(O)OH; or
  (3) one, two or three times substituted with alkyl, which alkyl is:
    (A) optionally interrupted one, two, or three times by —O—, —S(O)hd x-, —S(O)$_2$NH—, —NHS(O)$_2$—, —C(O)—NH—, —NH—C(O)—, or —P(O)(CH$_3$)—; and
    (B) unsubstituted or one, two or three times substituted with —OH, —NH$_2$, —C(O)OH, or —P(O)(CH$_3$)$_2$; or
  (4) once substituted with —C(O)OH and one, two or three times substituted with alkyl, which alkyl is:
    (A) optionally interrupted one, two, or three times by —O—, —S(O)$_x$—, —S(O)$_2$NH—, —NHS(O)$_2$—, —C(O)—NH—, —NH—C(O)—, or —P(O)(CH$_3$)—; and
    (B) unsubstituted or one, two or three times substituted with —OH, —NH$_2$, —C(O)OH, or —P(O)(CH$_3$)$_2$;
(b) pyrazolyl, which is:
  (1) unsubstituted; or
  (2) once substituted with —C(O)OH; or
  (3) one, two or three times substituted with alkyl, which alkyl is:
    (A) optionally interrupted one, two, or three times by —O—, —S(O)$_x$—, —S(O)$_2$NH—, —NHS(O)$_2$—, —C(O)—NH—, —NH—C(O)—, or —P(O)(CH$_3$)—; and
    (B) unsubstituted or one, two or three times substituted with —OH, —NH$_2$, —C(O)OH, or —P(O)(CH$_3$)$_2$; or
  (4) once substituted with —C(O)OH and one, two or three times substituted with alkyl, which alkyl is:
    (A) optionally interrupted one, two, or three times by —O—, —S(O)$_x$—, —S(O)$_2$NH—, —NHS(O)$_2$—, —C(O)—NH—, —NH—C(O)—, or —P(O)(CH$_3$)—; and
    (B) unsubstituted or one, two or three times substituted with —OH, —NH$_2$, —C(O)OH, or —P(O)(CH$_3$)$_2$;
(c) triazolyl, which is:
  (1) unsubstituted; or
  (2) once substituted with —C(O)OH; or
  (3) one, two or three times substituted with alkyl, which alkyl is:
    (A) optionally interrupted one, two, or three times by —O—, —S(O)$_x$—, —S(O)$_2$NH—, —NHS(O)$_2$—, —C(O)—NH—, —NH—C(O)—, or —P(O)(CH$_3$)—; and
    (B) unsubstituted or one, two or three times substituted with —OH, —NH$_2$, —C(O)OH, or —P(O)(CH$_3$)$_2$; or
  (4) once substituted with —C(O)OH and one, two or three times substituted with alkyl, which alkyl is:
    (A) optionally interrupted one, two, or three times by —O—, —S(O)$_x$—, —S(O)$_2$NH—, —NHS(O)$_2$—, —C(O)—NH—, —NH—C(O)—, or —P(O)(CH$_3$)—; and
    (B) unsubstituted or one, two or three times substituted with —OH, —NH$_2$, —C(O)OH, or —P(O)(CH$_3$)$_2$; and (d) tetrazolyl, which is:
  (1) unsubstituted; or
  (2) once substituted with —C(O)OH; or
  (3) one, two or three times substituted with alkyl, which alkyl is:
    (A) optionally interrupted one, two, or three times by —O—, —S(O)$_x$—, —S(O)$_2$NH—, —NHS(O)$_2$—, —C(O)—NH—, —NH—C(O)—, or —P(O)(CH$_3$)—; and
    (B) unsubstituted or one, two or three times substituted with —OH, —NH$_2$, —C(O)OH, or —P(O)(CH$_3$)$_2$; or
  (4) once substituted with —C(O)OH and one, two or three times substituted with alkyl, which alkyl is:
    (A) optionally interrupted one, two, or three times by —O—, —S(O)$_x$—, —S(O)$_2$NH—, —NHS(O)$_2$—, —C(O)—NH—, —NH—C(O)—, or —P(O)(CH$_3$)—; and
    (B) unsubstituted or one, two or three times substituted with —OH, —NH$_2$, —C(O)OH, or —P(O)(CH$_3$)$_2$;

n is 1, 2 or 3; and
x is 0, 1 or 2.

* * * * *

UNITED STATES PATENT AND TRADEMARK OFFICE
CERTIFICATE OF CORRECTION

PATENT NO. : 7,405,231 B2  
APPLICATION NO. : 11/073065  
DATED : July 29, 2008  
INVENTOR(S) : Bossenmaier et al.

Page 1 of 1

It is certified that error appears in the above-identified patent and that said Letters Patent is hereby corrected as shown below:

TITLE PAGE and Col. 1:
• The Title reads "OXIDIZED THIOETHER DERIVATIVES". The Title should read -- NOVEL OXIDIZED THIOETHER DERIVATIVES --.

Signed and Sealed this

Thirteenth Day of January, 2009

JON W. DUDAS  
*Director of the United States Patent and Trademark Office*

UNITED STATES PATENT AND TRADEMARK OFFICE
CERTIFICATE OF CORRECTION

PATENT NO. : 7,405,231 B2 Page 1 of 1
APPLICATION NO. : 11/073065
DATED : July 29, 2008
INVENTOR(S) : Birgit Bossenmaier et al.

It is certified that error appears in the above-identified patent and that said Letters Patent is hereby corrected as shown below:

Title Page,
Item [54], Title, the word "NOVEL" (as inserted by Certificate of Correction issued January 13, 2009) should be deleted and title is to be reinstated to read -- OXIDIZED THIOETHER DERIVATIVES --.

Signed and Sealed this

Third Day of February, 2009

JOHN DOLL
*Acting Director of the United States Patent and Trademark Office*